US010426777B2

(12) United States Patent
Tran et al.

(10) Patent No.: US 10,426,777 B2
(45) Date of Patent: Oct. 1, 2019

(54) METHODS USED TO TREAT CANCER

(71) Applicants: THE TRANSLATIONAL GENOMICS RESEARCH INSTITUTE, Phoenix, AZ (US); MAYO FOUNDATION FOR MEDICAL EDUCATION AND RESEARCH, Rochester, MN (US)

(72) Inventors: Nhan Tran, Phoenix, AZ (US); Joseph C. Loftus, Scottsdale, AZ (US); Harshil Dhruv, Phoenix, AZ (US)

(73) Assignees: The Translational Genomics Research Institute, Phoenix, AZ (US); Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/842,846

(22) Filed: Dec. 14, 2017

(65) Prior Publication Data

US 2018/0092922 A1    Apr. 5, 2018

Related U.S. Application Data

(60) Division of application No. 15/068,890, filed on Mar. 14, 2016, now Pat. No. 9,872,857, which is a continuation-in-part of application No. 14/595,423, filed on Jan. 13, 2015, now Pat. No. 9,283,195, which is a continuation of application No. 13/846,056, filed on Mar. 18, 2013, now abandoned, which is a division of application No. 12/911,091, filed on Oct. 25, 2010, now abandoned.

(60) Provisional application No. 62/145,040, filed on Apr. 9, 2015, provisional application No. 61/254,615, filed on Oct. 23, 2009.

(51) Int. Cl.
| | |
|---|---|
| *A61K 31/522* | (2006.01) |
| *A61K 31/00* | (2006.01) |
| *A61K 31/495* | (2006.01) |
| *A61K 31/713* | (2006.01) |
| *A61K 45/06* | (2006.01) |
| *C12Q 1/6886* | (2018.01) |
| *G01N 33/574* | (2006.01) |

(52) U.S. Cl.
CPC .......... *A61K 31/522* (2013.01); *A61K 31/00* (2013.01); *A61K 31/495* (2013.01); *A61K 31/713* (2013.01); *A61K 45/06* (2013.01); *C12Q 1/6886* (2013.01); *G01N 33/57411* (2013.01); *C12Q 2600/106* (2013.01); *C12Q 2600/158* (2013.01); *G01N 2800/52* (2013.01); *G01N 2800/54* (2013.01)

(58) Field of Classification Search
CPC .... A61K 31/00; A61K 31/495; A61K 31/522; A61K 31/713; A61K 45/06; G01N 33/57411; G01N 2800/52; G01N 2800/54; C12Q 1/6886; C12Q 2600/106; C12Q 2600/158
See application file for complete search history.

(56) References Cited

U.S. PATENT DOCUMENTS

| | | | |
|---|---|---|---|
| 2003/0186313 | A1 | 10/2003 | Fuqua et al. |
| 2005/0112558 | A1 | 5/2005 | Lo et al. |
| 2011/0091487 | A1 | 4/2011 | Spanjaard |
| 2014/0193406 | A1 | 7/2014 | Tran |

FOREIGN PATENT DOCUMENTS

WO    2008085601 A2    7/2008

OTHER PUBLICATIONS

Markman, M. (Jun. 1997). Cleveland Clinic Journal of Medicine. 64(6):331-333.*
Mariani, L., et al. Glioma cell motility is associated with reduced transcription of proapoptotic and proliferation genes: a cDNA microarray analysis. J Neurooncol 2001; 53(2):161-176.
Demuth, T., et al. MAP-ing glioma invasion: Mitogen-activated protein kinase kinase 3 and p38 drive glioma invasion and progression and predict patient survival. Mol Cancer Ther 2007; 6(4):1212-1222.
Ohnishi, T., et al. A novel model of glioma cell invasion using organotypic brain slice culture. Cancer Res 1998; 58(14)2935-2940.
Valster, A., et al. Cell migration and invasion assays. Methods 2005; 37(2):208-215.
Nakada, M., et al. EphB2/R-Ras signaling regulates glioma cell adhesion, growth, and invasion. Am J Pathol 2005; 167(2):565-576.
Moores, S. L, et al. Vav family proteins couple to diverse cell surface receptors. Mol Cell Biol 2000; 20(17):6364-6373.
Gao, C., et al. A Pyk2-Vav1 complex is recruited to b3-adhesion sites to initiate Rho activation. Biochem J 2009; 420(1):49-56.
Baker, S. D., et al. Absorption, metabolism, and excretion of 14C-temozolomide following oral administration to patients with advanced cancer. Clinical Cancer Research 1999; 5(2):309-317.
Stevens, M. F. G., et al. Antitumor activity and pharmacokinetics in mice of 8-carbamoyl-3-methyl-imidazo[5,1-d]-1,2,3,5-tetrazin-4(3H)-one (CCRG 81045; M & B 39831), a novel drug with potential as an alternative to dacarbazine. Cancer Res 1987; 47(22):5846-5852.
Pispa, J., et al. Edar and Troy signalling pathways act redundantly to regulate initiation of hair follicle development. Hum Mol Genet 2008; 17(21):3380-3391.
Tran, N., et al. The TROY Receptor is Overexpressed in Human Gliobastoma Multiforme and Fosters Glioma Cell Migration and Tumor Cell Survival. 98th AACR Annual Meeting, Poster Presentations. 2007, Abstract No. 1360. [Retrieved from the Internet on Jul. 20, 2018; <URL: http://cancerres.aacrjournals.org/content/67/9_Supplement/1360>].

(Continued)

Primary Examiner — Robert S Landsman
(74) Attorney, Agent, or Firm — Rodney J. Fuller; Booth Udall Fuller, PLC

(57) ABSTRACT

The invention encompasses methods of treating a patient with cancer, such as glioblastoma. The methods may include the administration of one or more pharmaceutical compositions that are capable of inhibiting TROY to treat the patient with cancer.

14 Claims, 28 Drawing Sheets

Specification includes a Sequence Listing.

(56) References Cited

OTHER PUBLICATIONS

Strausberg, et al. Tumor Necrosis Factor Receptor Superfamily, Member 19 [Homo Sapiens]. GenBank Direct Submission Accession AAH47321. Jul. 15, 2006 [Retrieved from the Internet on Jul. 26, 2018; <URL: http://ncbi.nlm.nih.gov/protein/28704107>].
Lucio-Eterovic, A. K., et al. Mediators of Glioblastoma Resistance and Invasion during Antivascular Endothelial Growth Factor Therapy. Clin Cancer Res 2009; 15(14):4589-4599.
Hisaoka, T., et al. Expression of a member of tumor necrosis factor receptor superfamily, TROY, in the developing mouse brain. Developmental Brain Research 2003; 143:105-109.
Hanley, J. A., et al. The Meaning and Use of the Area under a Receiver Operating Characteristic (ROC) Curve. Radiology 1982; 143:29-36.
Berens, M. E., et al.". . . those left behind." Biology and oncology of invasive glioma cells. Neoplasia 1999; 1(3):208-219.
Papenfuss, K., et al. Death receptors as targets for anti-cancer therapy. J Cell Mol Med 2008;12(6B):2566-2588.
Raftlopoulou, M., et al.Cell migration: Rho GTPases lead the way. Dev Biol 2004; 265(1):23-32.
Hall, A. Rho GTPases and the actin cytoskeleton. Science 1998; 279(5350):509-514.
Sahai, E., et al. 127. RHO-GTPases and cancer. Nat Rev Cancer 2002; 2(2):133-142.
Symons, M., et al. Rho family GTPases: more than simple switches. Trends Cell Biol 2000; 10(10):415-419.
Burridge, K., et al. Rho and Rac take center stage. Cell 2004;116(2):167-179.
Hwang, S. L., et al. The expression of rac1 pseudogene in human tissues and in human brain tumors. Eur Surg Res 2005; 37(2):100-104.
Iwadate, Y., et al. Proteome-based identification of molecular markers predicting chemosensitivity to each category of anticancer agents in human gliomas. Int J Oncol 2005; 26(4):993-998.
Salhia, B., et al. Inhibition of Rho-kinase affects astrocytoma morphology, motility, and invasion through activation of Rac1. Cancer Res 2005; 65(19):8792-8800.
Schmitz, A. A., et al. Rho GTPases: signaling, migration, and invasion. Exp Cell Res 2000; 261(1):1-12.
Yamaguchi, H., et al. Cell migration in tumors. Curr Opin Cell Biol 2005; 17(5):559-564.
Girault, J., et al. FAK and PYK2/CAKbeta in the nervous system: a link between neuronal activity, plasticity and survival? Trends Neurosci 1999; 22(6):257-263.
Avraham, H., et al. RAFTK/Pyk2-mediated cellular signalling. Cell Signal 2000; 12(3):123-133.
Bernstein, E., et al. The rest is silence. RNA 2001; 7(11):1509-1521.
Sun, C. K., et al. Proline-rich tyrosine kinase 2 (Pyk2) promotes proliferation and invasiveness of hepatocellular carcinoma cells through c-Src/ERK activation. Carcinogenesis 2008; 29(11):2096-2105.
Shi, Z., et al. Erlotinib (Tarceva, OSI-774) antagonizes ATP-binding cassette subfamily B member 1 and ATP-binding cassette subfamily G member 2 mediated drug resistance. Cancer Res 2007; 67(22):11012-11020.
Mani, S. A., et al. The epithelial-mesenchymal transition generates cells with properties of stem cells. Cell 2008;133(4):704-715.
Roelle, S., et al. Essential role of Pyk2 and Src kinase activation in neuropeptide-induced proliferation of small cell lung cancer cells. Oncogene 2007; 27(12):1737-1748.
Behmoaram, E., et al. Focal adhesion kinase-related proline-rich tyrosine kinase 2 and focal adhesion kinase are co-overexpressed in early-stage and invasive ErbB-2-positive breast cancer and cooperate for breast cancer cell tumorigenesis and invasiveness. Am J Pathol 2008; 173(5):1540-1550.
Bittner, M., et al. Molecular classification of cutaneous malignant melanoma by gene expression profiling. Nature 2000; 406(6795):536-540.

Hecker, T. P., et al. Overexpression of FAK promotes Ras activity through the formation of a FAK/p120RasGAP complex in malignant astrocytoma cells. Oncogene 2004; 23(22):3962-3971.
Giese, A., et al. Contrasting migratory response of astrocytoma cells to tenascin mediated by different integrins. J Cell Sci 1996; 109 (Pt 8):2161-2168.
Gutenberg, A., et al. Expression of tyrosine kinases FAK and Pyk2 in 331 human astrocytomas. Acta Neuropathol 2004; 108(3):224-230.
Van Der Horst, E H., et al. Tyrosine phosphorylation of PYK2 mediates heregulin-induced glioma invasion: novel heregulin/HER3-stimulated signaling pathway in glioma. Int J Cancer 2005; 113(5):689-698.
Loftus, J. C., et al. The Pyk2 FERM domain as a target to inhibit glioma migration. Mol Can Ther 2009; 8(6):1505-1514.
Tran, N. L., et al. The human Fn14 receptor gene is up-regulated in migrating glioma cells in vitro and overexpressed in advanced glial tumors. Am J Pathol 2003; 162(4):1313-1321.
Han, S., et al. TNF-related weak inducer of apoptosis receptor, a TNF receptor superfamily member, activates NF-kappa B through TNF receptor-associated factors. Biochem Biophys Res Commun 2003; 305(4):789-796.
Saitoh, T., et al. TWEAK induces NF-kB2 p100 processing and long lasting NF-kB activation. J Biol Chem 2003; 278(38):36005-36012.
Salhai, B., et al. The guanine nucleotide exchange factors trio, Ect2, and Vav3 mediate the invasive behavior of glioblastoma. Am J Pathol 2008; 173(6)1828-1838.
Berrier, A. L., et al. Activated R-Ras, Rac1, PI 3-Kinase and PKCe can each restore cell spreading inhibited by isolated integrin b1 cytoplasmic domains. J Cell Biol 2000; 151(7):1549-1560.
Ader, I., et al. Inhibition of Rho pathways induces radiosensitization and oxygenation in human glioblastoma xenografts. Oncogene 2003; 22(55):8861-8869.
Kukushima, Y., et al. Integrin alpha3 beta1-mediated interaction with laminin-5 stimulates adhesion, migration and invasion of malignant glioma cells. Int J Cancer 1998; 76(1):63-72.
Meyer, A. N., et al. The cytoplasmic tyrosine kinase Pyk2 as a novel effector of fibroblast growth factor receptor 3 activation. J Biol Chem 2004; 279(27):28450-28457.
Lozupone, F., et al. Identification and relevance of the CD95-binding domain in the N-terminal region of Ezrin. J Biol Chem 2004; 279(10):9199-9207.
Giannini, C., et al. Patient tumor EGFR and PDGFRA gene amplifications retained in an invasive intracranial xenograft model of glioblastoma multiforme. Neuro-Oncol.2005; 7(2):164-176.
Dunn, G. P., et al. Emerging insights into the molecular and cellular basis of glioblastoma. Genes Dev 2012; 26(8):756-784.
Taylor, T. E.,et al. Targeting EGFR for treatment of glioblastoma: molecular basis to overcome resistance. Curr Cancer Drug Targets. 2012; 12(3):197-209.
Ciardiello, F., et al. EGFR antagonists in cancer treatment. N Engl J Med 2008; 358(11):1160-1174.
Pao, W., et al. Rational, biologically based treatment of EGFR-mutant non-small-cell lung cancer. Nat Rev Cancer 2010; 10(11):760-774.
Hegi, M. E., et al. Pathway analysis of glioblastoma tissue after preoperative treatment with the EGFR tyrosine kinase inhibitor gefitinib—a phase II trial. Mol Cancer Ther 2011; 10(6):1102-1112.
Hegi, M. E., et al. Epidermal growth factor receptor: a re-emerging target in glioblastoma. Curr Opin Neurol. 2012; 25(6):774-779.
Yung, et al. Safety and efficacy of erlotinib in first-relapse glioblastoma: a phase II open-label study. Neuro Oncol 2010; 12(10):1061-1070.
Vivanco, I., et al. Differential sensitivity of glioma—versus lung cancer-specific EGFR mutations to EGFR kinase inhibitors. Cancer Discov. 2012; 2(5):458-471.
Belda-Iniesta, C., et al. Molecular biology of malignant gliomas. Clin Transl Oncol. 2006; 8(9):635-641.
Furnari, F. B., et al. Malignant astrocytic glioma: genetics, biology, and paths to treatment. Genes Dev 2007; 21(21):2683-2710.
Hayden, M. S., et al. NF-kB, the first quarter-century: remarkable progress and outstanding questions. Genes Dev 2012; 26(3):203-234.

(56) References Cited

OTHER PUBLICATIONS

Sarkaria, J. N., et al. Use of an orthotopic xenograft model for assessing the effect of epidermal growth factor receptor amplification on glioblastoma radiation response. Clin Cancer Res 2006; 12(7 Pt 1):2264-2271.
Carlson, B. L., et al. Radiosensitizing effects of temozolomide observed in vivo only in a subset of O6-methylguanine-DNA methyltransferase methylated glioblastoma multiforme xenografts. Int J Rad Oncol Biol Phys 2009; 75(1):212-219.
Mineo, J., et al. Low HER2-expressing glioblastomas are more often secondary to anaplastic transformation of low-grade glioma. J Neurooncol 2007; 85(3):281-287.
Schlegel, J., et al. Amplification and differential expression of members of the erbB-gene family in human glioblastoma. J Neurooncol 1994; 22(3):201-207.
Andersson, U., et al. Epidermal growth factor receptor family (EGFR, ErbB2-4) in gliomas and meningiomas. Acta Neuropathol 2004;1 08(2):135-142.
Carrasco-Garcia, E., et al. Small tyrosine kinase inhibitors interrupt EGFR signaling by interacting with erbB3 and erbB4 in glioblastoma cell lines. Exp Cell Res 2011; 317(10):1476-1489.
Torp, S. H., et al. Coexpression of c-erbB 1-4 receptor proteins in human glioblastomas. An immunohistochemical study. J Exp Clin Cancer Res 2007; 26(3):353-359.
Verhaak, R. G. W., et al. Integrated genomic analysis identifies clinically relevant subtypes of glioblastoma characterized by abnormalities in PDGFRA, IDH1, EGFR, and NF1. Cancer Cell 2010; 17(1):98-110.
Clark, P. A., et al. Activation of multiple ERBB family receptors mediates glioblastoma cancer stem-like cell resistance to EGFR-targeted inhibition. Neoplasia 2012; 14(5):420-428.
Baulida, J., et al. All ErbB receptors other than the epidermal growth factor receptor are endocytosis impaired. J Biol Chem 1996; 271(9):5251-5257.
Lenferink, A. E. G., et al. Differential endocytic routing of homo- and hetero-dimeric ErbB tyrosine kinases confers signaling superiority to receptor heterodimers. EMBO Journal 1998; 17(12):3385-3397.
Olayioye, M. A., et al. The ErbB signaling network: receptor heterodimerization in development and cancer. EMBO Journal 2000;1 9(13):3159-3167.
Oda, K., et al. A comprehensive pathway map of epidermal growth factor receptor signaling. Mol Syst Biol 2005; 1:2005.0010.
Yarden, Y., et al. Untangling the ErbB signalling network. Nat Rev Mol Cell Biol 2001; 2(2):127-137.
Ward, C. W.,et al. Insulin and epidermal growth factor receptors contain the cysteine repeat motif found in the tumor necrosis factor receptor. Proteins 1995; 22(2):141-153.
Banner, D. W., et al. Crystal structure of the soluble human 55 kd TNF receptor-human TNF beta complex: implications for TNF receptor activation. Cell 1993; 73(3):431-445.
Gan, H. K., et al. The EGFRvIII variant in glioblastoma multiforme. J Clin Neurosci 2009; 16(6):748-754.
Li, S., et al. Structural basis for inhibition of the epidermal growth factor receptor by cetuximab. Cancer Cell 2005; 7(4):301-311.
Ogiso, H., et al. Crystal structure of the complex of human epidermal growth factor and receptor extracellular domains. Cell 2002; 110(6):775-787.
Shan, Y., et al. Oncogenic mutations counteract intrinsic disorder in the EGFR kinase and promote receptor dimerization. Cell 2012; 149(4):860-870.
Ivkovic, S., et al. Direct inhibition of myosin II effectively blocks glioma invasion in the presence of multiple motogens. Mol Biol Cell 2012; 23(4):533-542.
Carter, R. E., et al. Endocytosis of functional epidermal growth factor receptor-green fluorescent protein chimera. J Biol Chem 1998; 273(52):35000-35007.
Huang, H. S., et al. The enhanced tumorigenic activity of a mutant epidermal growth factor receptor common in human cancers is mediated by threshold levels of constitutive tyrosine phosphorylation and unattenuated signaling. J Biol Chem 1997; 272(5):2927-2935.
Schmidt, M. H. H., et al. Epidermal growth factor receptor signaling intensity determines intracellular protein interactions, ubiquitination, and internalization. Proc Natl Acad Sci USA 2003; 100(11):6505-6510.
Ben-Kasus, T., et al. Persistent elimination of ErbB-2/HER2-overexpressing tumors using combinations of monoclonal antibodies: relevance of receptor endocytosis. Proc Natl Acad Sci USA 2009; 106(9):3294-3299.
Acevedo, V. D., et al. Inducible FGFR-1 activation leads to irreversible prostate adenocarcinoma and an epithelial-to-mesenchymal transition. Cancer Cell 2007; 12(6):559-571.
Amara, J. F., et al. A versatile synthetic dimerizer for the regulation of protein-protein interactions. Proc Natl Acad Sci USA 1997; 94(20):10618-10623.
Ruan, W., et al. A novel juxtamembrane domain in Tumor Necrosis Factor Receptor superfamily molecules activates Rac1 and controls neurite growth. Mol Biol Cell 2008; 19(8):3192-3202.
Jaffe, A., et al. Rho GTPases: biochemistry and biology. Annu Rev Cell Dev Biol 2005; 21:247-269.
Helzinger, D. B., et al. Gene expression profile of glioblastoma multiforme invasive phenotype points to new therapeutic targets. Neoplasia 2005; 7(1):7-16.
Lipinski, C. A., et al. Differential role of proline-rich tyrosine kinase 2 and focal adhesion kinase in determining glioblastoma migration and proliferation. Mol Cancer Res 2003; 1(5):323-332.
Lipinski, C. A., et al. Critical role of the FERM domain in Pyk2 stimulated glioma cell migration. Biochem Biophys Res Commun 2006; 349(3):939-947.
Lipinski, C. A., et al. The tyrosine kinase Pyk2 promotes migration and invasion of glioma cells. Neoplasia 2005; 7(5):435-445.
Rossman, K. L., et al. GEF means go: turning on Rho GTPases with guanine nucleotide-exchange factors. Nat Rev Mol Cell Biol 2005; 6(2):167-180.
Schiller, M. R. Coupling receptor tyrosine kinases to Rho GTPases-GEFs what's the link. Cell Signal 2006 ;18(11):1834-1843.
Chikumi, H., et al. Regulation of G protein-linked guanine nucleotide exchange factors for Rho, PDZ-RhoGEF, and LARG by tyrosine phosphorylation: evidence of a role for focal adhesion kinase. J Biol Chem 2002; 277(14):12463-12473.
Fortin, S. P., et al. Tumor necrosis factor-like weak inducer of apoptosis stimulation of glioma cell survival is dependent on Akt2 function. Mol Cancer Res 2009; 7(11):1871-1881.
Tran, N. L., et al. The tumor necrosis factor-like weak inducer of apoptosis (TWEAK)—fibroblast growth factor-inducible 14 (Fn14) signaling system regulates glioma cell survival via NF-kB pathway activation and BCL-XL/BCL-W expression. J Biol Chem 2005; 280(5):3483-3492.
Kislin, K. L., et al. NHERF-1: modulator of glioblastoma cell migration and invasion. Neoplasia 2009; 11(4):377-387.
Garcia-Mata, R., et al. Analysis of activated GAPs and GEFs in cell lysates. Methods Enzymol 2006; 406:425-437.
Tatsumoto, T., et al. Human ECT2 is an exchange factor for Rho GTPases, phosphorylated in G2/M phases, and involved in cytokinesis. J Cell Biol 1999; 147(5):921-928.
Solski, P. A., et al. Requirement for C-terminal sequences in regulation of Ect2 guanine nucleotide exchange specificity and transformation. J Biol Chem 2004; 279(24):25226-25233.
Movilla, N., et al. Biological and regulatory properties of Vav-3, a new member of the Vav family of oncoproteins. Mol Cell Biol 1999; 19(11):7870-7885.
Yiin, J. J., et al. Slit2 inhibits glioma cell invasion in the brain by suppression of Cdc42 activity. Neuro Oncol 2009; 11(6):779-789.
Guo, F., et al. Rho GTPase Cdc42 is essential for B lymphocyte development and activation. Blood 2009; 114(14):2909-2916.
Kononen, J., et al. Tissue microarrays for high-throughput molecular profiling of tumor specimens. Nat Med 1998; 4(7):844-847.
Lugli, A., et al. EphB2 expression across 138 human tumor types in a tissue microarray: high levels of expression in gastrointestinal cancers. Clin Cancer Res 2005; 11(18):6450-6458.

(56) References Cited

OTHER PUBLICATIONS

Chou, T., et al. Quantitative analysis of dose-effect relationships: the combined effects of multiple drugs or enzyme inhibitors. Adv Enzyme Regul 1984; 22:27-55.
Lim, Y., et al. PyK2 and FAK connections to p190Rho guanine nucleotide exchange factor regulate RhoA activity, focal adhesion formation, and cell motility. J Cell Biol 2008; 180(1)187-203.
Stupp, R., et al. Radiotherapy plus concomitant and adjuvant temozolomide for glioblastoma. N Engl J Med 2005; 352(10):987-996.
Dickins, R. A., et al. Probing tumor phenotypes using stable and regulated synthetic microRNA precursors. Nat Genet 2005; 37(11):1289-1295.
Stegmeier, F., et al. A lentiviral microRNA-based system for single-copy polymerase II-regulated RNA interference in mammalian cells. Proc Natl Acad Sci USA 2005; 102(37):13212-1321.
Wiznerowicz, M., et al. Conditional suppression of cellular genes: lentivirus vector-mediated drug-inducible RNA interference. J Virol 2003; 77(16):8957-8961.
Mansuy, I. M., et al. Restricted and regulated overexpression reveals calcineurin as a key component in the transition from short-term to long-term memory. Cell 1998; 92(1):39-49.
Yu, C. C., et al. The assessment of cellular proliferation by immunohistochemistry: a review of currently available methods and their applications. Histochemical Journal 1992; 24:121-131.
Stratagene Catalog 1988; p. 39.
Robbins, et al. Basic Pathology. 1976; 2d Ed.; W.B. Saunders Co., Philadelphia; pp. 68-90.
Dolecek, T. A., et al. CBTRUS Statistical Report: Primary Brain and Central Nervous System Tumors Diagnosed in the United States in 2005-2009. Neuro Oncol 2012; 14(Suppl 5): v1-v49.
McDonald, David R. New frontiers in the treatment of malignant glioma. Semin Oncol 2003; 30(6 Suppl 19):72-76.
Salhia, B., et al. Molecular pathways triggering glioma cell invasion. Expert Rev Mol Diagn 2006; 6(4):613-626.
Giese, A., et al. Cost of migration: invasion of malignant gliomas and implications for treatment. J Clin Oncol 2003; 21(8):1624-1636.
Hu, S., et al. Characterization of TNFRSF19, a novel member of the tumor necrosis factor receptor superfamily. Genomics 1999; 62(1):103-107.
Park, J. B., et al. A TNF receptor family member, TROY, is a coreceptor with Nogo receptor in mediating the inhibitory activity of myelin inhibitors. Neuron 2005; 45(3):345-351.
Pispa, J., et al. Ectodysplasin, Edar and TNFRSFI9 are expressed in complementary and overlapping patterns during mouse embryogenesis. Gene Expr Patterns 2003; 3(5):675-9.
Hisaoka, T., et al. Expression of a member of tumor necrosis factor receptor superfamily, TROY, in the developing olfactory system. Glia. 2004;45(4):313-324.
Shao, Z, et al. TAJ/TROY, an orphan TNF receptor family member, binds Nogo-66 receptor 1 and regulates axonal regeneration. Neuron 2005; 45(3):353-359.
Maher, E. A., et al. Malignant glioma: genetics and biology of a grave matter. Genes Dev 2001; 15(11):1311-1333.
Castro, M. G., et al. Current and future strategies for the treatment of malignant brain tumors. Pharmacol Ther 2003; 98(1):71-108.
Rich, J. N., et al. Development of novel targeted therapies in the treatment of malignant glioma. Nat Rev Drug Discov 2004; 3(5):430-446.
Bredel, M., et al. A network model of a cooperative genetic landscape in brain tumors. JAMA 2009; 302(3):261-275.
Parsons, D. W., et al. An Integrated Genomic Analysis of Human Glioblastoma Multiforme. Science 2008; 321(5897):1807-1812.
Lesniak, M. S., et al. Targeted therapy for brain tumours. Nat Rev Drug Discov 2004; 3(6):499-508.
Tysnes, B. B., et al. Biological mechanisms of glioma invasion and potential therapeutic targets. J Neurooncol 2001; 53(2):129-147.
Friedl, P., et al. Tumour-cell invasion and migration: diversity and escape mechanisms. Nat Rev Cancer 2003; 3(5):362-374.

Joy, A. M., et al. Migrating glioma cells activate the PI3-K pathway and display decreased susceptibility to apoptosis. J Cell Sci 2003; 116(21):4409-4417.
Eby, M. T., et al. TAJ, a novel member of the tumor necrosis factor receptor family, activates the c-Jun N-terminal kinase pathway and mediates caspase-independent cell death. J Biol Chem 2000; 275(20):15336-15342.
Spanjaard, R. A., et al. Tumor necrosis factor receptor superfamily member TROY is a novel melanoma biomarker and potential therapeutic target. Int J Cancer 2007; 120(6):1304-1310.
Chan, A. Y. et al. Roles of the Rac1 and Rac3 GTPases in human tumor cell invasion. Oncogene 2005; 24(53):7821-7829.
Chuang, Y., et al. Role of Synaptojanin 2 in Glioma Cell Migration and Invasion. Cancer Res 2004; 64(22):8271-8275.
Tran, N. L., et al. Increased fibroblast growth factor-inducible 14 expression levels promote glioma cell invasion via Rac1 and nuclear factor-kB and correlate with poor patient outcome. Cancer Res 2006; 66(19):9535-9542.
Nakada, M., et al. Ephrin-B3 ligand promotes glioma invasion through activation of Rac1. Cancer Res 2006; 66(17):8492-8500.
Lipinski, C. A., et al. Extended survival of Pyk2 or FAK deficient orthotopic glioma xenografts. J Neurooncol 2008 ;90(2)181-189.
Berens, M. E., et al. The role of extracellular matrix in human astrocytoma migration and proliferation studied in a microliter scale assay. Clin Exp Metastasis 1994; 12(6):405-415.
McDonough, W. S., et al. Regulation of glioma cell migration by serine-phosphorylated P311. Neoplasia 2005; 7(9):862-872.
Hashimoto, T., et al. Troy binding to lymphotoxin-alpha activates NF kappa B mediated transcription. Cell Cycle 2008; 7(1):106-111.
Jarzynka, M. J., et al. ELMO1 and Dock180, a bipartite Rac1 guanine nucleotide exchange factor, promote human glioma cell invasion. Cancer Res 2007; 67(15):7203-7211.
Taillandier, L., et al. . Models for neuro-oncological preclinical studies: solid orthotopic and heterotopic grafts of human gliomas into nude mice. J Neurosci Methods 2003;125(1-2)147-157.
Wilcox, M. E., et al. Reovirus as an oncolytic agent against experimental human malignant gliomas. J Natl Cancer Inst 2001; 93(12):903-912.
Mahesparan, R., et al. Expression of extracellular matrix components in a highly infiltrative in vivo glioma model. Acta Neuropathol 2003;105(1):49-57.
Sarkaria, J. N., et al. Identification of molecular characteristics correlated with glioblastoma sensitivity to EGFR kinase inhibition through use of an intracranial xenograft test panel. Mol Cancer Ther 2007; 6(3):1167-1174.
Pandita, A., et al. Contrasting in vivo and in vitro fates of glioblastoma cell subpopulations with amplified EGFR. Genes Chromosomes Cancer 2004; 39(1):29-36.
Mielke, R., et al. Propentofylline in the treatment of vascular dementia and Alzheimer-type dementia: overview of phase I and phase II clinical trials. Alzheimer Dis Assoc Disord 1998; 12(Suppl 2):S29-S35.
Rother, M., et al, Propentofylline in the treatment of Alzheimer's disease and vascular dementia: a review of phase III trials. Dement Geriatr Congn Disord 1998; 9(Suppl 1):36-43.
Sweitzer, et al. Propentofylline: glial modulation, neuroprotection, and alleviation of chronic pain. Handb Exp Pharmacol 2011; (200):235-250.
Jacobs, V. L., et al. Propentofylline decreases tumor growth in a rodent model of glioblastoma multiforme by a direct mechanism on microglia. Neuro Oncol 2012; 14(2):119-131.
Jacobs, V. L., et al. Propentofylline targets TROY, a novel microglial signaling pathway. PLoS One. 2012; 7(5): e37955.
Kamada, H., et al. Up-regulation of NFG, trkA, Fas, Down-Regulation of bc-2, and Induction of Apoptosis by Propentofylline in Human Glioma Cell Lines. No Oo Shinkei (Brain and Nerve) 1996; 48(11):1022-1028.
Stupp, R., et al. Effects of radiotherapy with concomitant and adjuvant temozolomide versus radiotherapy alone on survival in glioblastoma in a randomised phase III study: 5-year analysis of the EORTC-NCIC trial. Lancet Oncol 2009; 10(5):459-466.

(56) References Cited

OTHER PUBLICATIONS

Bei, J., et al. A genome-wide association study of nasopharyngeal carcinoma identifies three new susceptibility loci. Nat Genet 2010; 42(7):599-603.

Hu, Z., et al. A genome-wide association study identifies two new lung cancer susceptibility loci at 13q12.12 and 22q12.2 in Han Chinese. Nat Genet 2011; 43(8):792-796.

Schon, S., et al. beta-catenin regulates NF-kB activity via TNFRSF19 in colorectal cancer cells. Int J Cancer 2014; 135:1800-1811.

Paulino, V.M., et al. TROY (TNFRSF19) is overexpressed in advanced glial tumors and promotes glioblastoma cell invasion via Pyk2-Rac1 signaling. Mol Cancer Res 2010; 8(11)1558-1567.

Loftus, J. C., et al. TROY (TNFRSFI9) promotes glioblastoma survival signaling and therapeutic resistance. Mol Cancer Res 2013; 11(8):865-874.

Chan, F. K., et al. A domain in TNF receptors that mediates ligand-independent receptor assembly and signaling. Science 2000; 288(5475):2351-2354.

Locksley, R. M., et al. The TNF and TNF receptor superfamilies: integrating mammalian biology. Cell 2001; 104(4):487-501.

Nesvizhskii, A. I., et al. A statistical model for identifying proteins by tandem mass spectrometry. Anal Chem 2003; 75(17):4646-4658.

\* cited by examiner

FIG. 24A
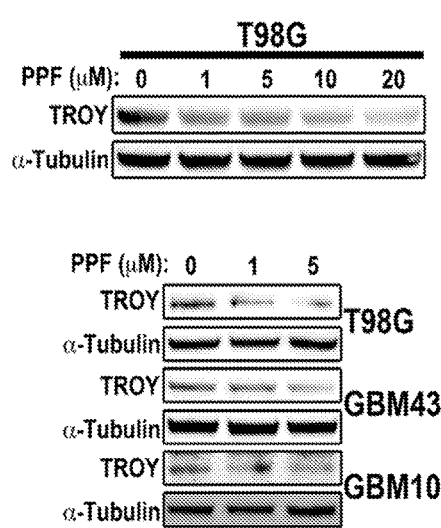
FIG. 24B
FIG. 24C
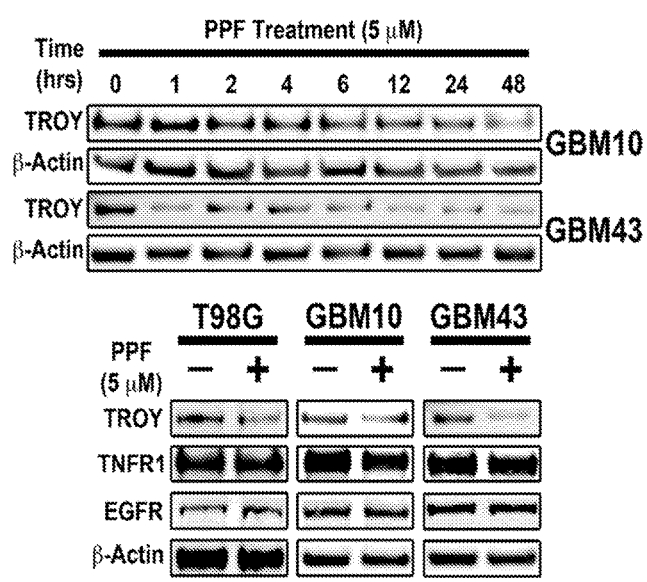
FIG. 24D

FIG. 26A
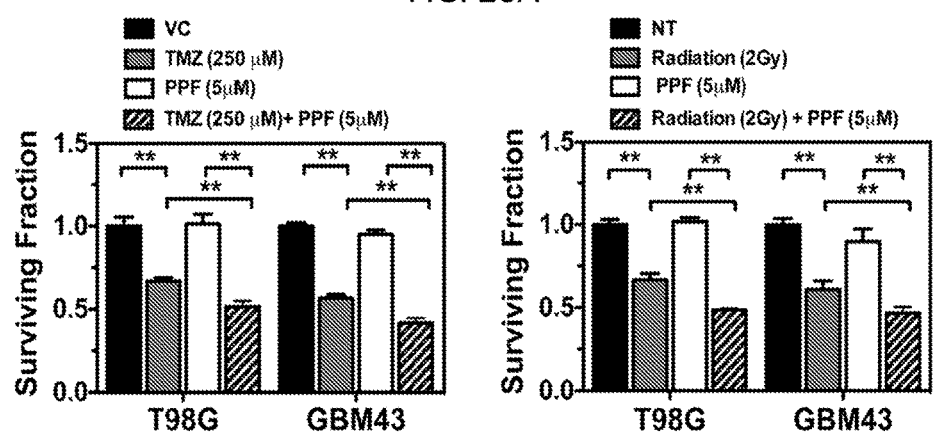
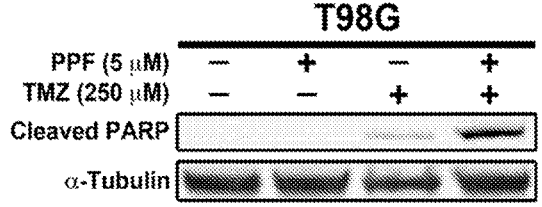
FIG. 26B
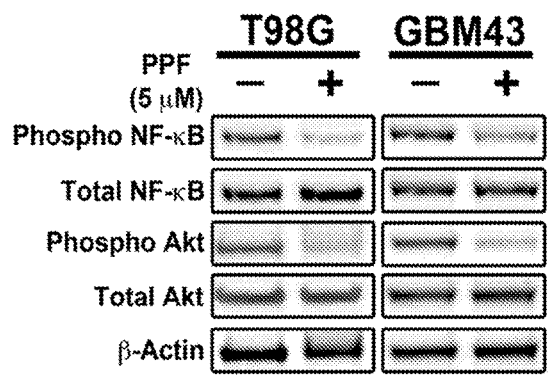
FIG. 26C

SEQUENCE LISTING

```
<160> NUMBER OF SEQ ID NOS: 4

<210> SEQ ID NO 1
<211> LENGTH: 4283
<212> TYPE: DNA
<213> ORGANISM: Homo Sapiens

<400> SEQUENCE: 1
gggagggtaa ctacctgctg aaagtgaact ttctttgata tccatgcata tatataaact      60
cagccctgcc tttgatgttc agcaactgat tcactgatca gattacaggc atttcatctc     120
cctgctcgtc tgcctttgat ctgcatggtt aattttattt tcctggattt gaagtttcgt     180
ctgggcttgt gctgacatac attttgga aggtagaagc atttggcaca gaagtgctgc       240
caggagaaac taagttgctg aacggaactc tccaacaata aatacatttg ataagaaaga     300 tggcttttaaa agtgctacta gaacaagaga aaacgttttt cactcttttta gtattactag   360 gctatttgtc atgtaaagtg acttgtgaat caggagactg tagacagcaa gaattcaggg     420
atcggtctgg aaactgtgtt ccctgcaacc agtgtgggcc aggcatggag ttgtctaagg     480
aatgtggctt cggctatggg gaggatgcac agtgtgtgac gtgccggctg cacaggttca     540
aggaggactg gggcttccag aaatgcaagc cctgtctgga ctgcgcagtg gtgaaccgct     600 tcagaaggc aaattgttca gccaccagtg atgccatctg cggggactgc ttgccaggat      660
tttataggaa gacgaaactt gtcggctttc aagacatgga gtgtgtgcct tgtggagacc     720
ctcctcctcc ttacgaaccg cactgtgcca gcaaggtcaa cctcgtgaag atcgcgtcca     780
cggcctccag cccacgggac acggcgctgg ctgccgttat ctgcagcgct ctggccaccg     840
tcctgctggc cctgctcatc ctctgtgtca tctattgtaa gagacagttt atggagaaga     900 acccagctg gtctctgcgg tcacaggaca ttcagtacaa cggctctgag ctgtcgtgtt     960
ttgacagacc tcagctccac gaatatgccc acagagcctg ctgccagtgc cgccgtgact    1020
cagtgcagac ctgcgggccg gtgcgcttgc tcccatccat gtgctgtgag gaggcctgca    1080
gccccaaccc ggcgactctt ggttgtgggg tgcattctgc agccagtctt caggcaagaa    1140
acgcaggccc agccggggag atggtgccga ctttcttcgg atccctcacg cagtccatct    1200
gtggcgagtt ttcagatgcc tggcctctga tgcagaatcc catgggtggt gacaacatct    1260
```

-continued

```
cttttttgtga ctcttatcct gaactcactg gagaagacat tcattctctc aatccagaac    1320
ttgaaagctc aacgtctttg gattcaaata gcagtcaaga tttggttggt ggggctgttc    1380
cagtccagtc tcattctgaa aactttacag cagctactga tttatctaga tataacaaca    1440
cactggtaga atcagcatca actcaggatg cactaactat gagaagccag ctagatcagg    1500
agagtggtgc tgtcatccac ccagccactc agacgtccct ccaggaagct aaagaacct     1560 gcttctttct gcagtagaag cgtgtgctgg aacccaaaga gtactccttt gttaggctta    1620
tggactgagc agtctggacc ttgcatggct tctggggcaa aaataaatct gaaccaaact    1680
gacggcattt gaagcctttc agccagttgc ttctgagcca gaccagctgt aagctgaaac    1740
ctcaatgaat aacaagaaaa gactccaggc cgactcatga tactctgcat ctttcctaca    1800
tgagaagctt ctctgccaca aaagtgactt caaagacgga tgggttgagc tggcagccta    1860
tgagattgtg gacatataac aagaaacaga aatgccctca tgcttatttt catggtgatt    1920
gtggttttac aagactgaag acccagagta tactttttct ttccagaaat aatttcatac    1980
cgcctatgaa atatcagata aattaccttga gcttttatgt agaatgggtt caaaagtgag    2040
tgtttctatt tgagaaggac acttttttcat catctaaact gattcgcata ggtggttaga    2100
atggccctca tattgcctgc ctaaatcttg ggtttattag atgaagttta ctgaatcaga    2160
ggaatcagac agaggaggat agctctttcc agaatccaca cttctgacct cagcctcggt    2220
ctcatgaaca cccgctgatc tcaggagaac acctgggcta gggaatgtgg tcgagaaagg    2280
gcagcccatt gcccagaatt aacacatatt gtagagactt gtatgcaaag gttggcatat    2340
ttatatgaaa attagttgct atagaaacat ttgttgcatc tgtccctctg cctgagctta    2400
gaaggttata gaaaagggt atttataaac ataaatgacc ttttacttgc attgtatctt     2460
atactaaagg ctttagaaat tacaacatat caggttcccc tactactgaa gtagccttcc    2520
gtgagaacac accacatgtt aggactagaa gaaaatgcac aatttgtagg ggtttggatg    2580
aagcagctgt aactgcccta gtgtagtttg accaggacat tgtcgtgctc cttccaattg    2640
tgtaagatta gttagcacat catctcctac tttagccatc cggtgttgga tttaagagga    2700
cggtgcttct ttctattaaa gtgctccatc ccctaccatc tacacattag cattgtctct    2760
agagctaaga cagaaattaa ccccgttcag tcacaaagca gggaatggtt catttactct    2820
taatctttat gccctggaga agacctactt gaacagggca tatttttag acttctgaac     2880 atcagtatgt tcgagggtac tatgatattt tggtttggaa ttgccctgcc caagtcactg    2940
tcttttaact tttaaactga atattaaaat gtatctgtct ttcctagtat gttttatct     3000 tctcatgtat tatccatggt tttctctgtt tgtgacagat tagtaaaatt taatgagccc    3060
tctttcttgt ggccgtttct ccatagtttt aggttttgat atgtgtttac tagcttgcct    3120
gtgtctggta catctcatga cctcaattcc ctcacctgaa ataggaaatg agaatgtttc    3180
attgtagccc caagcggtca tgtcaaccta gtgcctagtc ataattaatt gacttttcct    3240
gtattacttc tttttttaag tataaaccaa tgatcctttg gtagtcaaga actcttagga    3300
acattgcctt ttggacatgt aaaatattta ggatttgacc acacaatggc tatgaaaatg    3360
caagtagttt cctcgcgtga cctcaccatg attcacatac gtgccactgt ttgaaatctg    3420
gtctgtttgc atttctgtta tgacagagag atgatgtttg catttctgtt atgacagaga    3480
gatgatgaaa gtaggcaggg ctgtgttcct ttgtgtagcc tgtatatatt ttccatatgt    3540
agagccctga ttaacttcaa ggacaaacac tggctggaga aagccagact gatgggaatg    3600
```

-continued

```
agactttggc caaaaatccc aaaacatcat tttcaatcag tagagaagtg cttagggttg    3660
aaaattgatt tcatttgcta ctgaatttgg taaatcctgg gtaactttta tcaagatgaa    3720
gacattttac cctacctact ctagaaatat acaacaatgt tatattttac actccttgga    3780
aacatttgag gaaaaaaatg caatttgcac ttcactttgt tggaatatcc catagcactc    3840
aataaactca gctgctagag tgccgatgtc aggagggctg tgtcgggtaa tgcgtgtggc    3900
tgaatgggca taaccactgt ggcttcttgt gctgcagaag ctcgttgaca agactgagga    3960
ggatttcaag agcaaccaag taaagtcatg aattttctaa ttttgtgtat atggaatata    4020
tttttaaata gagattttc tactttagat aatgtgttaa tattgctatt acctaggtta    4080
agcactattg tctgtgctag taagaaaaag aaaggaaaac catcattgct ttatagtagc    4140
ttatatcaat ttagatttca tcattactat tttgcatact ggaatttata aatgtgtaaa    4200
ttatcatttt cttagttttg taataccttt tttatttgtg aataaaatta tcacctggta    4260
ttcttaaaaa aaaaaaaaaa aaa                                             4283
```

<210> SEQ ID NO 2
<211> LENGTH: 417
<212> TYPE: PRT
<213> ORGANISM: Homo Sapiens

<400> SEQUENCE: 2

```
Met Ala Leu Lys Val Leu Leu Glu Gln Glu Lys Thr Phe Phe Thr Leu
1               5                   10                  15

Leu Val Leu Leu Gly Tyr Leu Ser Cys Lys Val Thr Cys Glu Ser Gly
            20                  25                  30

Asp Cys Arg Gln Gln Glu Phe Arg Asp Arg Ser Gly Asn Cys Val Pro
        35                  40                  45

Cys Asn Gln Cys Gly Pro Gly Met Glu Leu Ser Lys Glu Cys Gly Phe
    50                  55                  60

Gly Tyr Gly Glu Asp Ala Gln Cys Val Thr Cys Arg Leu His Arg Phe
65                  70                  75                  80

Lys Glu Asp Trp Gly Phe Gln Lys Cys Lys Pro Cys Leu Asp Cys Ala
                85                  90                  95

Val Val Asn Arg Phe Gln Lys Ala Asn Cys Ser Ala Thr Ser Asp Ala
            100                 105                 110

Ile Cys Gly Asp Cys Leu Pro Gly Phe Tyr Arg Lys Thr Lys Leu Val
        115                 120                 125

Gly Phe Gln Asp Met Glu Cys Val Pro Cys Gly Asp Pro Pro Pro
    130                 135                 140

Tyr Glu Pro His Cys Ala Ser Lys Val Asn Leu Val Lys Ile Ala Ser
145                 150                 155                 160

Thr Ala Ser Ser Pro Arg Asp Thr Ala Leu Ala Val Ile Cys Ser
                165                 170                 175

Ala Leu Ala Thr Val Leu Leu Ala Leu Leu Ile Leu Cys Val Ile Tyr
            180                 185                 190

Cys Lys Arg Gln Phe Met Glu Lys Lys Pro Ser Trp Ser Leu Arg Ser
        195                 200                 205

Gln Asp Ile Gln Tyr Asn Gly Ser Glu Leu Ser Cys Phe Asp Arg Pro
    210                 215                 220

Gln Leu His Glu Tyr Ala His Arg Ala Cys Cys Gln Cys Arg Arg Asp
225                 230                 235                 240

Ser Val Gln Thr Cys Gly Pro Val Arg Leu Leu Pro Ser Met Cys Cys
                245                 250                 255
```

```
Glu Glu Ala Cys Ser Pro Asn Pro Ala Thr Leu Gly Cys Gly Val His
            260                 265                 270
Ser Ala Ala Ser Leu Gln Ala Arg Asn Ala Gly Pro Ala Gly Glu Met
            275                 280                 285
Val Pro Thr Phe Phe Gly Ser Leu Thr Gln Ser Ile Cys Gly Glu Phe
            290                 295                 300
Ser Asp Ala Trp Pro Leu Met Gln Asn Pro Met Gly Gly Asp Asn Ile
305                 310                 315                 320
Ser Phe Cys Asp Ser Tyr Pro Glu Leu Thr Gly Glu Asp Ile His Ser
                    325                 330                 335
Leu Asn Pro Glu Leu Glu Ser Ser Thr Ser Leu Asp Ser Asn Ser Ser
                340                 345                 350
Gln Asp Leu Val Gly Gly Ala Val Pro Val Gln Ser His Ser Glu Asn
            355                 360                 365
Phe Thr Ala Ala Thr Asp Leu Ser Arg Tyr Asn Asn Thr Leu Val Glu
            370                 375                 380
Ser Ala Ser Thr Gln Asp Ala Leu Thr Met Arg Ser Gln Leu Asp Gln
385                 390                 395                 400
Glu Ser Gly Ala Val Ile His Pro Ala Thr Gln Thr Ser Leu Gln Glu
                    405                 410                 415
Ala

<210> SEQ ID NO 3
<211> LENGTH: 22
<212> TYPE: DNA
<213> ORGANISM: Homo Sapiens

<400> SEQUENCE: 3
ggccaaaaat cccaaaacat ca                                      22

<210> SEQ ID NO 4
<211> LENGTH: 22
<212> TYPE: DNA
<213> ORGANISM: Homo Sapiens

<400> SEQUENCE: 4
ccacagtggt tatgcccatt ca                                      22
```

METHODS USED TO TREAT CANCER

CROSS-REFERENCE TO RELATED APPLICATIONS

This application is a divisional of U.S. patent application Ser. No. 15/068,890, filed Mar. 14, 2016 (published as U.S. 20150220571), which claims the benefit of U.S. Provisional Application No. 62/145,040, filed Apr. 9, 2015, and is a continuation-in-part of U.S. patent application Ser. No. 14/595,423, filed Jan. 13, 2015 (issued as U.S. Pat. No. 9,283,195), which is a continuation of U.S. patent application Ser. No. 13/846,056, filed Mar. 18, 2013, now abandoned, which is a divisional of U.S. patent application Ser. No. 12/911,091, filed Oct. 25, 2010, now abandoned, which claims the benefit of U.S. Provisional Application No. 61/254,615, filed Oct. 23, 2009, the contents each of which are incorporated herein and are not admitted to be prior art with respect to the present invention by the mention in this cross-reference section.

STATEMENT REGARDING FEDERALLY SPONSORED RESEARCH

This invention was made with government support under NS086853 and CA108961 awarded by the National Institutes of Health. The government has certain rights in this invention.

REFERENCE TO SEQUENCE LISTING SUBMITTED ELECTRONICALLY

The official copy of the sequence listing is submitted electronically via EFS-Web as an ASCII-formatted sequence listing with a file named "Seq_List.txt" created on Mar. 14, 2016, and having a size of 10,097 bytes, and is filed concurrently with the specification. The sequence listing contained in this ASCII-formatted document is part of the specification and is herein incorporated by reference in its entirety.

BACKGROUND OF THE INVENTION

Glioblastoma multiforme (GBM) is the most malignant form of all primary adult brain tumors (See Reference 1) Although significant technical advances in surgical and radiation treatment for brain tumors have emerged, their impact on clinical outcome for patients has been only modest (See References 2-4). Of the features that characterize GBM, arguably none is more clinically significant than the propensity of glioma cells to infiltrate into normal brain tissue. These invasive cells render complete resection impossible and confer resistance to chemo- and radiation-therapy. Thus, improved treatment of malignant glioma awaits a way of targeting the dispersing tumor cells in the CNS.

BRIEF SUMMARY OF THE INVENTION

Some embodiments of the invention may include a method of treating a patient with cancer. For example, in some aspect, the method may include the step of administering a therapeutically effective amount of a first pharmaceutical composition to the patient with cancer. In some embodiments, the first pharmaceutical composition may include propentofylline or a pharmaceutically acceptable salt and the cancer may be glioblastoma (e.g., invasive glioblastoma). Moreover, the first pharmaceutical composition may include one or more pharmaceutically acceptable carriers. In some embodiments, the methods of the current invention may also include the administration of a second pharmaceutical composition, which may further comprise at least one of the following: TROY inhibitors, Pyk2 inhibitors, Rac1 inhibitors, Dock180 inhibitors, Dock7 inhibitors, temozolomide and bevacizumab. In some embodiments, the method may also include the administration of therapeutically effective amounts of radiation to the patient. In addition, in some aspects, the second pharmaceutical composition may be co-administered to the patient. Moreover, in some embodiments, the second pharmaceutical composition may comprise the administration of radiation to the patient with cancer.

Some embodiments of the invention provide a method of treating glioblastoma cells (e.g., invasive glioblastoma cells) in a subject. The method may include the steps of contacting the glioblastoma cells with a therapeutically effective amount of propentofylline or a pharmaceutically acceptable salt thereof and further contacting the glioblastoma cells with a pharmaceutical composition. In some aspects, the pharmaceutical composition may comprise the administration of one or more compounds selected from the group consisting of Pyk2 inhibitors, Rac1 inhibitors, Dock180 inhibitors, Dock7 inhibitors, temozolomide and bevacizumab. In other aspects, the method of may include the pharmaceutical composition comprising a therapeutically effective amount of radiation. Moreover, in some embodiments, the method may include sequentially contacting the glioblastoma cells with the therapeutically effective amount of propentofylline or a pharmaceutically acceptable salt thereof and the pharmaceutical composition. Alternatively, in some embodiments, the method may include substantially simultaneously contacting the glioblastoma cells with the therapeutically effective amount of propentofylline or a pharmaceutically acceptable salt thereof and the pharmaceutical composition.

Some embodiments may further comprise a pharmaceutical composition for the treatment of glioblastoma. The pharmaceutical composition may include a therapeutically effective amount of first active ingredient comprising propentofylline or a pharmaceutically acceptable salt thereof and a second active ingredient. By way of example only, the second active ingredient may comprise one or more compounds selected from the group consisting of Pyk2 inhibitors, Rac1 inhibitors, Dock180 inhibitors, Dock7 inhibitors, temozolomide and bevacizumab. Moreover, in some embodiments, the pharmaceutical composition may further comprise at least one pharmaceutically acceptable carrier.

BRIEF DESCRIPTION OF THE FIGURES

A more complete understanding of the present invention may be derived by referring to the detailed description when considered in connection with the following illustrative figures.

FIG. 10A depicts immunofluorescent staining for TROY in T98G cells using an anti-HA antibody. FIG. 10B depicts immunofluorescent staining for TROY in T98G-TROY-HA cells using an anti-HA antibody. FIG. 10C represents T98G-TROY-HA stained with secondary antibody alone. The arrows in FIG. 10B represent TROY staining at the membrane periphery and cellular extension.

FIGS. 24A-24D illustrate that PPF treatment decreases TROY expression in GBM cells. FIG. 24A—a Western blot analysis of TROY expression in T98G cells. Cells were treated with PPF at indicated concentrations for 6 hrs, lysed, and cell lysates immunoblotted with anti-TROY antibody. Immunoblotting of α-Tubulin in cell lysates is included as a loading control. FIG. 24B—Western blot analysis of TROY expression in T98G, GBM43, and GBM10 cells. Cells were treated with PPF at indicated concentrations for 24 hrs, lysed, and cell lysates immunoblotted with anti-TROY and α-Tubulin antibodies. FIG. 24C—Western Blot analysis of TROY expression in GBM10 and GBM43 primary glioma cells. Cells were treated with 5 μM PPF, lysed at the indicated time-points, and the lysates immunoblotted with an anti-TROY antibody. Immunoblotting of β-Actin in cell lysates is included as a loading control. FIG. 24D—Western Blot analysis of T98G, GBM10 and GBM43 glioma cells treated with 5 μM PPF for 24 hours. Lysates were immunoblotted with anti-TROY, anti-TNFR1, anti-EGFR, and β-Actin antibodies.

FIG. 25A—T98G, GBM43, and GBM10 cells were incubated with increasing concentrations of PPF (0, 5, 50, and 500 μM). After 0, 48, 96 and 144 hours of treatment, cell were trypsinized and counted using an automated cell counter. FIG. 24B—GBM43, GBM10, and T98G glioma cells were treated with increasing doses of PPF (0.5, 1, 5, 10, and 20 μM) in triplicate. The Cell Titer Glo (Promega) reagent was used to measure survival. Raw values were normalized on a plate-by-plate basis such that 100% cell viability was equivalent to the mean of vehicle wells and 0% cell viability was equivalent to the mean of the MG132 positive control. The normalized data was used to assess viability of glioma cells after PPF treatment.

FIGS. 26A-26C depict that PPF sensitizes GBM cells to TMZ and radiotherapy. FIG. 26A—A clonogenic assay was used to assess T98G and GBM43 cells survival after TMZ and radiation treatment. Cells were pre-treated with 5 μM PPF for 24 hours, and then either treated with 250 μM TMZ for 24 hours or exposed to 2 Gy radiation. Graph depicts the surviving fraction in the treated cells compared to vehicle (VC) treated or non-treated (NT) cells, **p<0.01. FIG. 26B—T98G glioma cells were treated with vehicle, PPF (5 μM), TMZ (250 μM), and PPF in combination with TMZ. TMZ-induced apoptosis was assayed by immunoblot analysis of cell lysates with an antibody to cleaved PARP. Immunoblotting for α-Tubulin was included as a loading control. FIG. 26C—T98G, GBM10, and GBM43 cells were treated with PPF (5 μM), lysed, and then immunoblotted to assess the activation of AKT and NF-κB. Immunoblotting for 3-Actin is included as a loading control.

FIG. 27A—T98G, GBM10, and GBM43 glioma cells were treated with 5 μM PPF and invasion was assayed over 24 hours utilizing a Matrigel invasion assay, *p<0.05. FIG. 27B—T98G glioma cells were serum starved, pre-incubated with 5 μM PPF or vehicle for 1 hour, and then stimulated with 10% FBS for 2-10 mins. Cell lysates were harvested and equal concentrations of protein were assessed for Rac1 activation.

FIG. 28A—GBM43 cells were preincubated with 5 μM PPF or vehicle for 1 hour prior to 10% FBS stimulation for 5 min. After FBS stimulation, cells were fixed, permeabilized, and stained for F-actin. For each experimental condition, at least 12 images were taken randomly. Arrowhead indicates membrane ruffles. FIG. 28B—Graph depicts the average lamellipodia in T98G, GBM10, and GBM43 cells in the presence or absence of 10% FBS with or without 5 μM PPF as indicated. Lamellipodia were traced using Image J software. For each cell, the fraction of the cell perimeter that displayed lamellipodia was calculated, *p<0.05.

Figure 1:
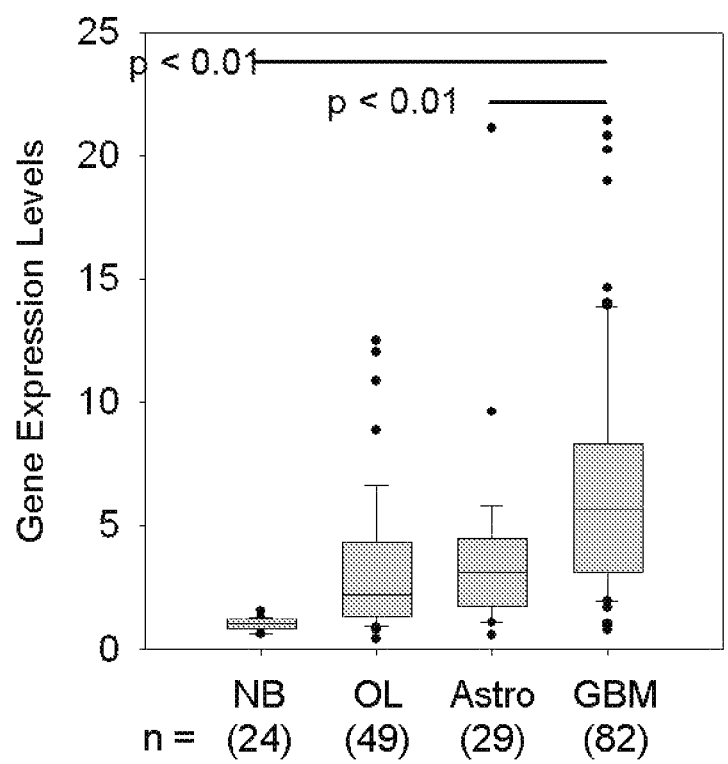
FIG. 1 depicts expression of TROY in normal brain and various glioblastoma types in the NCBI Gene Expression Omnibus GDS1962 dataset.

Elements and acts in the figures are illustrated for simplicity and have not necessarily been rendered according to any particular sequence or embodiment.

DETAILED DESCRIPTION OF THE INVENTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention.

Gliomas, primary brain tumors that derive from glial support cells, are the most common primary tumor of the adult central nervous system and will result in an estimated 13,000 deaths in 2010 (See References 1, 3, 11, and 12). Adult gliomas of astrocytic origin (astrocytomas) comprise a spectrum of neoplasms that are generally classified by WHO standards into low-grade benign tumors (i.e. juvenile pilocytic astrocytoma, diffuse astrocytoma) and high-grade malignant tumors (i.e. anaplastic astrocytoma and glioblastoma multiforme; GBM). Patients diagnosed with grade IV GBM, the most aggressive malignant glioma, have a median survival of 9-12 months after the onset of clinical symptoms (See References 11-13). Molecular analyses of glioma specimens have identified several common genetic alterations (e.g., p16INK4a deletion) and gene expression changes (e.g., EGFR overexpression) that may contribute to glioblastoma formation (See References 14 and 15).

In general, gliomas are extremely difficult to treat using conventional approaches (See References 12-16.) This is primarily due to the intrinsic propensity of glioma cells to exit the tumor core and invade the adjacent normal brain parenchyma (See References 3 and 4). These migrating cells escape surgical resection and are poorly targeted by radiation or chemotherapy. They sometimes travel over long distances, frequently along blood vessel and fiber tracts, and then initiate secondary tumor growth at their final destination. This distinguishing invasive ability is not shared by nonglial cells that metastasize from other primary tumor sites (e.g. breast) to brain tissue. The invasion of glioma cells is likely triggered by a presently undefined signal or signals that promote a cascade of cellular responses, including cell elongation, integrin-mediated cell attachment to extracellular matrix (ECM) molecules, the production and secretion of ECM-degrading enzymes, and cell movement (See References 17 and 18).

Migrating glioma cells exhibit decreased susceptibility to pro-apoptotic agents (See Reference 19) providing them with an additional mechanism for resisting current radiological and chemotherapeutic treatment modalities.

TROY (TNFRSF19) is an orphan member of the TNFR superfamily that is highly expressed in embryonic and adult CNS, and developing hair follicles (See References 5-10). During mouse embryogenesis, TROY mRNA is detected in many developing tissues including the limb buds, eyelids, whiskers, mammary glands, epidermis, bronchial, tongue, dental and gastric epithelium as well as the germinal zones of the CNS including the ventricular zone and subventricular zone. However, in adult animals, TROY expression changes and is primarily restricted to hair follicles and neuron-like cells in the cerebrum, cerebral cortex, developing olfactory system as well as dorsal root and retinal ganglion neurons (See References 5-10) In the peripheral nervous system, TROY functions as a co-receptor for the ligand-binding Nogo-66 receptor 1 (NgR1) to form the TROY/NgR1/LINGO complex that activates the RhoA pathway to inhibit neurite outgrowth of dorsal root ganglion neurons in adult mice (See References 6 and 9). In humans, TROY mRNA is primarily expressed in the brain and also the prostate, whereas low or undetectable levels are observed in the heart, lung, liver, thymus, uterus, skeletal muscle, spleen, colon testis, kidney and peripheral blood lymphocytes (See Reference 20). The reason or mechanism for this "switch-off" of TROY expression after birth is unclear, but its strict control indicates that aberrant expression may be detrimental. Indeed, it has been recently reported that TROY is highly expressed in primary and metastatic melanoma cells, but not in melanocytes found in normal skin biopsies and primary skin cell cultures (See Reference 21).

Herein, the Inventor demonstrates that TROY serves as a target or marker of invasive glioblastoma, that its expression is linked to poor therapeutic outcome and that it serves as a marker of resistance to temozolomide and as a marker of sensitivity to classes of drugs that treat glioblastoma by targeting pathways that contribute to glioma cell migration and invasion.

A marker may be any molecular structure produced by a cell, expressed inside the cell, accessible on the cell surface, or secreted by the cell. A marker may be any protein, carbohydrate, fat, nucleic acid, catalytic site, or any combination of these such as an enzyme, glycoprotein, cell membrane, virus, cell, organ, organelle, or any uni- or multimolecular structure or any other such structure now known or yet to be disclosed whether alone or in combination. A marker may also be called a target and the terms are used interchangeably.

A marker may be represented by the sequence of a nucleic acid from which it can be derived. Examples of such nucleic acids include miRNA, tRNA, siRNA, mRNA, cDNA, or genomic DNA sequences. While a marker may be represented by the sequence of a single nucleic acid strand (e.g. 5'→3'), nucleic acid reagents that bind the marker may also bind to the complementary strand (e.g. 3'→5'). Alternatively, a marker may be represented by a protein sequence. The concept of a marker is not limited to the products of the exact nucleic acid sequence or protein sequence by which it may be represented. Rather, a marker encompasses all molecules that may be detected by a method of assessing the expression of the marker.

Examples of molecules encompassed by a marker include point mutations, silent mutations, deletions, frameshift mutations, translocations, alternative splicing derivatives, differentially methylated sequences, differentially modified protein sequences, truncations, soluble forms of cell membrane associated markers, and any other variation that results in a product that may be identified as the marker. The following nonlimiting examples are included for the purposes of clarifying this concept: If expression of a specific marker in a sample is assessed by RTPCR, and if the sample expresses an mRNA sequence different from the sequence used to identify the specific marker by one or more nucleotides, but the marker may still be detected using RTPCR, then the specific marker encompasses the sequence present in the sample. Alternatively if expression of a specific marker in a sample is assessed by an antibody and the amino acid sequence of the marker in the sample differs from a sequence used to identify marker by one or more amino acids, but the antibody is still able to bind to the version of the marker in the sample, then the specific marker encompasses the sequence present in the sample.

Expression encompasses any and all processes through which material derived from a nucleic acid template may be produced. Expression thus includes processes such as RNA transcription, mRNA splicing, protein translation, protein folding, post-translational modification, membrane transport, associations with other molecules, addition of carbohydrate moieties to proteins, phosphorylation, protein complex formation and any other process along a continuum that results in biological material derived from genetic material whether in vitro, in vivo, or ex vivo. Expression also encompasses all processes through which the production of material derived from a nucleic acid template may be actively or passively suppressed. Such processes include all aspects of transcriptional and translational regulation. Examples include heterochromatic silencing, differential methylation, transcription factor inhibition, any form of RNAi silencing, microRNA silencing, alternative splicing, protease digestion, posttranslational modification, and alternative protein folding.

Expression may be assessed by any number of methods used to detect material derived from a nucleic acid template used currently in the art and yet to be developed. Examples of such methods include any nucleic acid detection method including the following nonlimiting examples, microarray analysis, RNA in situ hybridization, RNAse protection assay, Northern blot, reverse transcriptase PCR, quantitative PCR, quantitative reverse transcriptase PCR, quantitative real-time reverse transcriptase PCR, reverse transcriptase treatment followed by direct sequencing, direct sequencing of genomic DNA, or any other method of detecting a specific nucleic acid now known or yet to be disclosed. Other examples include any process of assessing protein expression including flow cytometry, immunohistochemistry, ELISA, Western blot, and immunoaffinity chromatography, HPLC, mass spectrometry, protein microarray analysis, PAGE analysis, isoelectric focusing, 2-D gel electrophoresis, or any enzymatic assay. Methods of detecting expression may include methods of purifying nucleic acid, protein, or some other material depending on the type of marker. Any method of nucleic acid purification may be used, depending on the type of marker. Examples include phenol alcohol extraction, ethanol extraction, guanidium isothionate extraction, gel purification, size exclusion chromatography, cesium chloride preparations, and silica resin preparation. Any method of protein purification may be used, also depending on the type of marker. Examples include size exclusion chromatography, hydrophobic interaction chromatography, ion exchange chromatography, affinity chromatography (including affinity chromatography of tagged proteins), metal binding, immunoaffinity chromatography, and HPLC.

Nucleic acid amplification is a process by which copies of a nucleic acid may be made from a source nucleic acid. Nucleic acids that may be subjected to amplification may be from any source. In some nucleic amplification methods, the copies are generated exponentially. Examples of nucleic acid amplification include but are not limited to: the polymerase chain reaction (PCR), ligase chain reaction (LCR), self-sustained sequence replication (3SR), nucleic acid sequence based amplification (NASBA), strand displacement amplification (SDA), amplification with Qβ replicase, whole genome amplification with enzymes such as φ29, whole genome PCR, in vitro transcription with any RNA polymerase, or any other method by which copies of a desired sequence are generated.

Polymerase chain reaction (PCR) is a particular method of amplifying DNA, generally involving the mixing of a nucleic sample, two or more primers, a DNA polymerase, which may be a thermostable DNA polymerase such as Taq or Pfu, and deoxyribose nucleoside triphosphates (dNTPs). In general, the reaction mixture is subjected to temperature cycles comprising a denaturation stage, (typically 80-100° C.) an annealing stage with a temperature that is selected based on the melting temperature (Tm) of the primers and the degeneracy of the primers, and an extension stage (for example 40-75° C.) In real-time PCR analysis, additional reagents, methods, optical detection systems, and devices are used that allow a measurement of the magnitude of fluorescence in proportion to concentration of amplified DNA. In such analyses, incorporation of fluorescent dye into the amplified strands may be detected or labeled probes that bind to a specific sequence during the annealing phase release their fluorescent tags during the extension phase. Either of these will allow a quantification of the amount of specific DNA present in the initial sample. Often, the result of a real-time PCR will be expressed in the terms of cycle threshold (Ct) values. The Ct represents the number of PCR cycles for the fluorescent signal from a real-time PCR reaction to cross a threshold value of fluorescence. Ct is inversely proportional to the amount of target nucleic acid originally present in the sample. RNA may be detected by PCR analysis by creating a DNA template from RNA through a reverse transcriptase enzyme.

Other methods used to assess expression include the use of natural or artificial ligands capable of specifically binding a marker. Such ligands include antibodies, antibody complexes, conjugates, natural ligands, small molecules, nanoparticles, or any other molecular entity capable of specific binding to a marker. Antibodies may be monoclonal, polyclonal, or any antibody fragment including an Fab, F(ab)$_2$, Fv, scFv, phage display antibody, peptibody, multispecific ligand, or any other reagent with specific binding to a marker. Ligands may be associated with a label such as a radioactive isotope or chelate thereof, dye (fluorescent or nonfluorescent), stain, enzyme, metal, or any other substance capable of aiding a machine or a human eye from differentiating a cell expressing a marker from a cell not expressing a marker. Additionally, expression may be assessed by monomeric or multimeric ligands associated with substances capable of killing the cell. Such substances include protein or small molecule toxins, cytokines, pro-apoptotic substances, pore forming substances, radioactive isotopes, or any other substance capable of killing a cell.

Differential expression encompasses any detectable difference between the expression of a marker in one sample relative to the expression of the marker in another sample. Differential expression may be assessed by a detector, an instrument containing a detector, or by aided or unaided human eye. Examples include but are not limited to differential staining of cells in an IHC assay configured to detect a marker, differential detection of bound RNA on a microarray to which a sequence capable of binding to the marker is bound, differential results in measuring RTPCR measured in the number of PCR cycles necessary to reach a particular optical density at a wavelength at which a double stranded DNA binding dye (e.g. SYBR Green) incorporates, differential results in measuring label from a reporter probe used in a real-time RTPCR reaction, differential detection of fluorescence on cells using a flow cytometer, differential intensities of bands in a Northern blot, differential intensities of bands in an RNAse protection assay, differential cell death measured by apoptotic markers, differential cell death measured by shrinkage of a tumor, or any method that allows a detection of a difference in signal between one sample or set of samples and another sample or set of samples.

The expression of the marker in a sample may be compared to a level of expression predetermined to predict the presence or absence of a particular physiological characteristic. The level of expression may be derived from a single control or a set of controls. A control may be any sample with a previously determined level of expression. A control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources. Comparison of the expression of the marker in the sample to a particular level of expression results in a prediction that the sample exhibits or does not exhibit the cellular or physiological characteristic.

Prediction of a cellular or physiological characteristic includes the prediction of any cellular or physiological state that may be predicted by assessing the expression of a marker. Examples include the identity of a cell as a particular cell including a particular normal or cancer cell type, the likelihood that one or more diseases is present or absent, the likelihood that a present disease will progress, remain unchanged, or regress, the likelihood that a disease will respond or not respond to a particular therapy, or any other outcome. Further examples include the likelihood that a cell will move, senesce, apoptose, differentiate, metastasize, or change from any state to any other state or maintain its current state.

Expression of a marker in a sample may be more or less than that of a level predetermined to predict the presence or absence of a cellular or physiological characteristic. The expression of the marker in the sample may be more than 1,000,000×, 100,000×, 10,000×, 1000×, 100×, 10×, 5×, 2×, 1×, 0.5×, 0.1× 0.01×, 0.001×, 0.0001×, 0.00001×, 0.000001×, 0.0000001× or less than that of a level predetermined to predict the presence or absence of a cellular or physiological characteristic.

The invention contemplates assessing the expression of the marker in any biological sample from which the expression may be assessed. One skilled in the art would know to select a particular biological sample and how to collect said sample depending upon the marker that is being assessed. Examples of sources of samples include but are not limited to biopsy or other in vivo or ex vivo analysis of prostate, breast, skin, muscle, facia, brain, endometrium, lung, head and neck, pancreas, small intestine, blood, liver, testes, ovaries, colon, skin, stomach, esophagus, spleen, lymph node, bone marrow, kidney, placenta, or fetus. In some aspects of the invention, the sample comprises a fluid sample, such as peripheral blood, lymph fluid, ascites, serous fluid, pleural effusion, sputum, cerebrospinal fluid, amniotic fluid, lacrimal fluid, stool, or urine. Samples include single cells, whole organs or any fraction of a whole organ, in any condition including in vitro, ex vivo, in vivo, post-mortem, fresh, fixed, or frozen.

One type of cellular or physiological characteristic is the risk that a particular disease outcome will occur. Assessing this risk includes the performing of any type of test, assay, examination, result, readout, or interpretation that correlates with an increased or decreased probability that an individual has had, currently has, or will develop a particular disease, disorder, symptom, syndrome, or any condition related to health or bodily state. Examples of disease outcomes include, but need not be limited to survival, death, progression of existing disease, remission of existing disease, initiation of onset of a disease in an otherwise disease-free subject, or the continued lack of disease in a subject in which there has been a remission of disease. Assessing the risk of a particular disease encompasses diagnosis in which the type of disease afflicting a subject is determined. Assessing the risk of a disease outcome also encompasses the concept of prognosis. A prognosis may be any assessment of the risk of disease outcome in an individual in which a particular disease has been diagnosed. Assessing the risk further encompasses prediction of therapeutic response in which a treatment regimen is chosen based on the assessment. Assessing the risk also encompasses a prediction of overall survival after diagnosis.

Determining the level of expression that signifies a physiological or cellular characteristic may be assessed by any of a number of methods. The skilled artisan will understand that numerous methods may be used to select a level of expression for a particular marker or a plurality of markers that signifies one or more particular physiological or cellular characteristics. In diagnosing the presence of a disease, a threshold value may be obtained by performing the assay method on samples obtained from a population of patients having a certain type of disease (cancer for example), and from a second population of subjects that do not have the disease. In assessing disease outcome or the effect of treatment, a population of patients, all of which have, a disease such as cancer, may be followed for a period of time. After the period of time expires, the population may be divided into two or more groups. For example, the population may be divided into a first group of patients whose disease progresses to a particular endpoint and a second group of patients whose disease does not progress to the particular endpoint. Examples of endpoints include disease recurrence, death, metastasis or other states to which disease may progress. If expression of the marker in a sample is more similar to the predetermined expression of the marker in one group relative to the other group, the sample may be assigned a risk of having the same outcome as the patient group to which it is more similar.

In addition, one or more levels of expression of the marker may be selected that signify a particular physiological or cellular characteristic. For example, Receiver Operating Characteristic curves, or "ROC" curves, may be calculated by plotting the value of a variable versus its relative frequency in two populations. For any particular marker, a distribution of marker expression levels for subjects with and without a disease may overlap. This indicates that the test does not absolutely distinguish between the two populations with complete accuracy. The area of overlap indicates where the test cannot distinguish the two groups. A threshold is selected. Expression of the marker in the sample above the threshold indicates the sample is similar to one group and expression of the marker below the threshold indicates the sample is similar to the other group. The area under the ROC curve is a measure of the probability that the expression correctly indicated the similarity of the sample to the proper group. See, e.g., Hanley et al., *Radiology* 143: 29-36 (1982) hereby incorporated by reference.

Additionally, levels of expression may be established by assessing the expression of a marker in a sample from one patient, assessing the expression of additional samples from the same patient obtained later in time, and comparing the expression of the marker from the later samples with the initial sample or samples. This method may be used in the case of markers that indicate, for example, progression or worsening of disease or lack of efficacy of a treatment regimen or remission of a disease or efficacy of a treatment regimen.

Other methods may be used to assess how accurately the expression of a marker signifies a particular physiological or cellular characteristic. Such methods include a positive likelihood ratio, negative likelihood ratio, odds ratio, and/or hazard ratio. In the case of a likelihood ratio, the likelihood that the expression of the marker would be found in a sample with a particular cellular or physiological characteristic is compared with the likelihood that the expression of the marker would be found in a sample lacking the particular cellular or physiological characteristic.

An odds ratio measures effect size and describes the amount of association or non-independence between two groups. An odds ratio is the ratio of the odds of a marker being expressed in one set of samples versus the odds of the marker being expressed in the other set of samples. An odds ratio of 1 indicates that the event or condition is equally likely to occur in both groups. An odds ratio grater or less than 1 indicates that expression of the marker is more likely to occur in one group or the other depending on how the odds ratio calculation was set up. A hazard ratio may be calculated by estimate of relative risk. Relative risk is the chance that a particular event will take place. It is a ratio of the probability that an event such as development or progression of a disease will occur in samples that exceed a threshold level of expression of a marker over the probability that the event will occur in samples that do not exceed a threshold level of expression of a marker. Alternatively, a hazard ratio may be calculated by the limit of the number of events per unit time divided by the number at risk as the time interval decreases. In the case of a hazard ratio, a value of 1 indicates that the relative risk is equal in both the first and second groups. A value greater or less than 1 indicates that the risk is greater in one group or another, depending on the inputs into the calculation.

Additionally, multiple threshold levels of expression may be determined. This can be the case in so-called "tertile," "quartile," or "quintile" analyses. In these methods, multiple groups can be considered together as a single population, and are divided into 3 or more bins having equal numbers of individuals. The boundary between two of these "bins" may be considered threshold levels of expression indicating a particular level of risk of a disease developing or signifying a physiological or cellular state. A risk may be assigned based on which "bin" a test subject falls into.

A subject includes any human or non-human mammal, including for example: a primate, cow, horse, pig, sheep, goat, dog, cat, or rodent, capable of developing cancer including human patients that are suspected of having cancer, that have been diagnosed with cancer, or that have a family history of cancer. Methods of identifying subjects suspected of having cancer include but are not limited to: physical examination, family medical history, subject medical history including exposure to environmental factors, biopsy, or any of a number of imaging technologies such as ultrasonography, computed tomography, magnetic resonance imaging, magnetic resonance spectroscopy, or positron emission tomography.

Cancer cells include any cells derived from a tumor, neoplasm, cancer, precancer, cell line, malignancy, or any other source of cells that have the potential to expand and grow to an unlimited degree. Cancer cells may be derived from naturally occurring sources or may be artificially created. Cancer cells may also be capable of invasion into other tissues and metastasis. Cancer cells further encompass any malignant cells that have invaded other tissues and/or metastasized. One or more cancer cells in the context of an organism may also be called a cancer, tumor, neoplasm, growth, malignancy, or any other term used in the art to describe cells in a cancerous state.

Examples of cancers that could serve as sources of cancer cells include solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Additional cancers that may serve as sources of cancer cells include blood borne cancers such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

The present invention further provides kits to be used in assessing the expression of a particular RNA in a sample from a subject to assess the risk of developing disease. Kits include any combination of components that facilitates the performance of an assay. A kit that facilitates assessing the expression of an RNA may include suitable nucleic acid-based and immunological reagents as well as suitable buffers, control reagents, and printed protocols.

Kits that facilitate nucleic acid based methods may further include one or more of the following: specific nucleic acids such as oligonucleotides, labeling reagents, enzymes including PCR amplification reagents such as Taq or Pfu; reverse transcriptase, or one or more other polymerases, and/or reagents that facilitate hybridization. Specific nucleic acids may include nucleic acids, polynucleotides, oligonucleotides (DNA, or RNA), or any combination of molecules that includes one or more of the above, or any other molecular entity capable of specific binding to a nucleic acid marker. In one aspect of the invention, the specific nucleic acid comprises one or more oligonucleotides capable of hybridizing to the marker.

A specific nucleic acid may include a label. A label may be any substance capable of aiding a machine, detector, sensor, device, or enhanced or unenhanced human eye from differentiating a sample that displays positive expression from a sample that displays reduced expression. Examples of labels include but are not limited to: a radioactive isotope or chelate thereof, a dye (fluorescent or nonfluorescent) stain, enzyme, or nonradioactive metal. Specific examples include but are not limited to: fluorescein, biotin, digoxigenin, alkaline phosphatase, biotin, streptavidin, $^3$H, $^{14}$C, $^{32}$P, $^{35}$S, or any other compound capable of emitting radiation, rhodamine, 4-(4'-dimethylaminophenylazo) benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraacetic acid ("EDTA") and derivatives thereof or any other compound that signals the presence of the labeled nucleic acid. In one embodiment of the invention, the label includes one or more dyes optimized for use in genotyping. Examples of such dyes include but are not limited to: dR110, 5-FAM, 6FAM, dR6G, JOE, HEX, VIC, TET, dTAMRA, TAMRA, NED, dROX, PET, and LIZ.

An oligonucleotide is a reagent capable of binding a nucleic acid sequence. An oligonucleotide may be any polynucleotide of at least 2 nucleotides. Oligonucleotides may be less than 10, less than 15, less than 20, less than 30, less than 40, less than 50, less than 75, less than 100, less than 200, less than 500, or more than 500 nucleotides in length. While oligonucleotides are often linear, they may, depending on their sequence and conditions, assume a two- or three-dimensional structure. Oligonucleotides may be chemically synthesized by any of a number of methods including sequential synthesis, solid phase synthesis, or any other synthesis method now known or yet to be disclosed. Alternatively, oligonucleotides may be produced by recombinant DNA based methods. One skilled in the art would understand the length of oligonucleotide necessary to perform a particular task. Oligonucleotides may be directly labeled, used as primers in PCR or sequencing reactions, or bound directly to a solid substrate as in oligonucleotide arrays.

A nucleotide is an individual deoxyribonucleotide or ribonucleotide base. Examples of nucleotides include but are not limited to: adenine, thymine, guanine, cytosine, and uracil, which may be abbreviated as A, T, G, C, or U in representations of oligonucleotide or polynucleotide sequence. Any molecule of two or more nucleotide bases, whether DNA or RNA, may be termed a nucleic acid.

An oligonucleotide used to detect to an allele may be affixed to a solid substrate. Alternatively, the sample may be affixed to a solid substrate and the nucleic acid reagent placed into a mixture. For example, the nucleic acid reagent may be bound to a substrate in the case of an array or the sample may be bound to a substrate as the case of a Southern Blot, Northern blot or other method that affixes the sample to a substrate. A nucleic acid reagent or sample may be covalently bound to the substrate or it may be bound by some non covalent interaction including electrostatic, hydrophobic, hydrogen bonding, Van Der Waals, magnetic, or any other interaction by which an oligonucleotide may be attached to a substrate while maintaining its ability to recognize the allele to which it has specificity. A substrate may be any solid or semi solid material onto which a probe may be affixed, attached or printed, either singly or in the formation of a microarray. Examples of substrate materials include but are not limited to polyvinyl, polysterene, polypropylene, polyester or any other plastic, glass, silicon dioxide or other silanes, hydrogels, gold, platinum, microbeads, micelles and other lipid formations, nitrocellulose, or nylon membranes. The substrate may take any shape, including a spherical bead or flat surface.

A nucleotide is an individual deoxyribonucleotide or ribonucleotide base. Examples of nucleotides include but are not limited to: adenine, thymine, guanine, cytosine, and uracil, which may be abbreviated as A, T, G, C, or U in representations of oligonucleotide or polynucleotide sequence.

In some aspects of the invention, the probe may be affixed to a solid substrate. In other aspects of the invention, the sample may be affixed to a solid substrate. A probe or sample may be covalently bound to the substrate or it may be bound by some non covalent interaction including electrostatic, hydrophobic, hydrogen bonding, Van Der Waals, magnetic, or any other interaction by which a probe such as an oligonucleotide probe may be attached to a substrate while maintaining its ability to recognize the allele to which it has specificity. A substrate may be any solid or semi solid material onto which a probe may be affixed, attached or printed, either singly or in the formation of a microarray. Examples of substrate materials include but are not limited to polyvinyl, polysterene, polypropylene, polyester or any other plastic, glass, silicon dioxide or other silanes, hydrogels, gold, platinum, microbeads, micelles and other lipid formations, nitrocellulose, or nylon membranes. The substrate may take any form, including a spherical bead or flat surface. For example, the probe may be bound to a substrate in the case of an array. The sample may be bound to a substrate as (for example) the case of Southern Blots, Northern blots or other method that affixes the sample to a substrate.

Kits may also contain reagents that detect proteins, often through the use of an antibody. These kits will contain one or more specific antibodies, buffers, and other reagents configured to detect binding of the antibody to the specific epitope. One or more of the antibodies may be labeled with a fluorescent, enzymatic, magnetic, metallic, chemical, or other label that signifies and/or locates the presence of specifically bound antibody. The kit may also contain one or more secondary antibodies that specifically recognize epitopes on other antibodies. These secondary antibodies may also be labeled. The concept of a secondary antibody also encompasses non-antibody ligands that specifically bind an epitope or label of another antibody. For example, streptavidin or avidin may bind to biotin conjugated to another antibody. Such a kit may also contain enzymatic substrates that change color or some other property in the presence of an enzyme that is conjugated to one or more antibodies included in the kit.

A kit may also contain an indication of a result of the use of the kit that signifies a particular physiological or cellular characteristic. An indication includes any guide to a result that would signal the presence or absence of any physiological or cellular state that the kit is configured to predict. For example, the indication may be expressed numerically, expressed as a color or density of a color, expressed as an intensity of a band, derived from a standard curve, or expressed in comparison to a control. The indication may be communicated through the use of a writing that may be contained physically in or on the kit (on a piece of paper for example), posted on the Internet, mailed to the user separately from the kit, or embedded in a software package. The writing may be in any medium that communicates how the result may be used to predict the cellular or physiological characteristic such as a printed document, a photograph, sound, color, or any combination thereof.

The invention further encompasses pharmaceutical compositions that include one or more active pharmaceutical agents as ingredients. By way of example only, in some aspects, the active pharmaceutical agent may comprise a TROY inhibitor, such as propentofylline (PPF) or pharmaceutically salts thereof. In other embodiments, the active pharmaceutical agent may comprise an epidermal growth factor receptor inhibitor, such as, but not limited to gefitinib, erlotinib, cetuximab, lapatinib, panitumumab, vandetanib, afatinib, icotinib, zalutumumab, nimotuzumab, and matuzumab or any combination thereof, including pharmaceutically acceptable salts.

According to some embodiments, PPF ((3-methyl-1-(5-oxohexyl)-7-propyl-3,7-dihydro-1H-purine-2,6-dione) is an atypical synthetic methylxanthine compound that has been studied extensively in preclinical models of CNS disorders and in Phase II and III clinical trials for Alzheimer's disease and vascular dementia (See References 37-38). These clinical trials revealed the therapeutic efficacy, blood brain barrier permeability, and a minimal side effect profile of PPF (See Reference 39). It has been demonstrated that systemic PPF treatment decreased tumor growth in a CNS-1 rat model via modulation of microglia (See Reference 40). PPF has been shown to inhibit the migration of microglia by decreasing TROY expression, thus suppressing the activation of downstream effector molecules, such as Pyk2 and Rac1 (See Reference 41). Targeting molecular drivers of glial cell invasion hampers the dispersion of GBM cells and enhances their vulnerability to adjuvant, chemo, and radiation therapy (See Reference 42). This application further incorporates by reference for all purposes the following non-patent literature: H. Dhruv et al., Journal of Neurooncology February 2016, Vol 126, pages 397-404.

Such pharmaceutical compositions may take any physical form necessary depending on a number of factors including the desired method of administration and the physicochemical and stereochemical form taken by the active pharmaceutical agent or pharmaceutically acceptable salts thereof. Such physical forms include a solid, liquid, gas, sol, gel, aerosol, or any other physical form now known or yet to be disclosed. The concept of a pharmaceutical composition including an active pharmaceutical agent also encompasses the active pharmaceutical agent without any other additive. The physical form of the invention may affect the route of administration and one skilled in the art would know to choose a route of administration that takes into consideration both the physical form of the active pharmaceutical agent and the disorder to be treated. Pharmaceutical compositions that include the active pharmaceutical agent may be prepared using methodology well known in the pharmaceutical art. A pharmaceutical composition that includes the active pharmaceutical agent may include a second effective compound of a distinct chemical formula from the active pharmaceutical agent. For example, in some embodiments, the pharmaceutical composition can include a combination of any of the aforementioned or later disclosed active pharmaceutical agents described in this instant application. This second effective compound may have the same or a similar molecular target as the target or it may act upstream or downstream of the molecular target of the active pharmaceutical agent with regard to one or more biochemical pathways.

Pharmaceutical compositions including the active pharmaceutical agent include materials capable of modifying the physical form of a dosage unit. In one nonlimiting example, the composition includes a material that forms a coating that holds in the active pharmaceutical agent. Materials that may be used in such a coating, include, for example, sugar, shellac, gelatin, or any other inert coating agent.

Pharmaceutical compositions including the active pharmaceutical agent may be prepared as a gas or aerosol. Aerosols encompass a variety of systems including colloids and pressurized packages. Delivery of a composition in this form may include propulsion of a pharmaceutical composition including the active pharmaceutical agent through use of liquefied gas or other compressed gas or by a suitable pump system. Aerosols may be delivered in single phase, bi-phasic, or tri-phasic systems.

In some aspects of the invention, the pharmaceutical composition including the active pharmaceutical agent is in the form of a solvate. Such solvates are produced by the dissolution of the active pharmaceutical agent in a pharmaceutically acceptable solvent. Pharmaceutically acceptable solvents include any mixtures of more than one solvent. Such solvents may include pyridine, chloroform, propan-1-ol, ethyl oleate, ethyl lactate, ethylene oxide, water, ethanol, and any other solvent that delivers a sufficient quantity of the disclosed compound to treat the affliction without serious complications arising from the use of the solvent in a majority of patients.

Pharmaceutical compositions that include the disclosed compound may also include a pharmaceutically acceptable carrier. Carriers include any substance that may be administered with the disclosed compound with the intended purpose of facilitating, assisting, or helping the administration or other delivery of the active pharmaceutical agent. Carriers include any liquid, solid, semisolid, gel, aerosol or anything else that may be combined with the active pharmaceutical agent to aid in its administration. Examples include diluents, adjuvants, excipients, water, oils (including petroleum, animal, vegetable or synthetic oils.) Such carriers include particulates such as a tablet or powder, liquids such as oral syrup or injectable liquid, and inhalable aerosols. Further examples include saline, gum acacia, gelatin, starch paste, talc, keratin, colloidal silica, and urea. Such carriers may further include binders such as ethyl cellulose, carboxymethylcellulose, microcrystalline cellulose, or gelatin; excipients such as starch, lactose or dextrins; disintegrating agents such as alginic acid, sodium alginate, Primogel, and corn starch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of carriers include polyethylene glycol, cyclodextrin, oils, or any other similar liquid carrier that may be formulated into a capsule. Still further examples of carriers include sterile diluents such as water for injection, saline solution, physiological saline, Ringer's solution, isotonic sodium chloride, fixed oils such as synthetic mono or diglycerides, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, thickening agents, lubricating agents, and coloring agents.

The pharmaceutical composition including the active pharmaceutical agent may take any of a number of formulations depending on the physicochemical form of the composition and the type of administration. Such forms include solutions, suspensions, emulsions, tablets, pills, pellets, capsules, capsules including liquids, powders, sustained-release formulations, directed release formulations, lyophylates, suppositories, emulsions, aerosols, sprays, granules, powders, syrups, elixirs, or any other formulation now known or yet to be disclosed. Additional examples of suitable pharmaceutical carriers are described in "Remington's Pharmaceutical Sciences" by E. W. Martin, hereby incorporated by reference in its entirety.

Methods of administration include, but are not limited to, oral administration and parenteral administration. Parenteral administration includes, but is not limited to intradermal, intramuscular, intraperitoneal, intravenous, subcutaneous, intranasal, epidural, sublingual, intranasal, intracerebral, intraventricular, intrathecal, intravaginal, transdermal, rectal, by inhalation, or topically to the ears, nose, eyes, or skin. Other methods of administration include but are not limited to infusion techniques including infusion or bolus injection, by absorption through epithelial or mucocutaneous linings such as oral mucosa, rectal and intestinal mucosa. Compositions for parenteral administration may be enclosed in ampoule, a disposable syringe or a multiple-dose vial made of glass, plastic or other material.

Administration may be systemic or local. Local administration is administration of the disclosed compound to the area in need of treatment. Examples include local infusion during surgery; topical application, by local injection; by a catheter; by a suppository; or by an implant. Administration may be by direct injection at the site (or former site) of a cancer, tumor, or precancerous tissue or into the central nervous system by any suitable route, including intraventricular and intrathecal injection. Intraventricular injection can be facilitated by an intraventricular catheter, for example, attached to a reservoir, such as an Ommaya reservoir. Pulmonary administration may be achieved by any of a number of methods known in the art. Examples include use of an inhaler or nebulizer, formulation with an aerosolizing agent, or via perfusion in a fluorocarbon or synthetic pulmonary surfactant. The disclosed compound may be delivered in the context of a vesicle such as a liposome or any other natural or synthetic vesicle.

A pharmaceutical composition formulated so as to be administered by injection may be prepared by dissolving the active pharmaceutical agent with water so as to form a solution. In addition, a surfactant may be added to facilitate the formation of a homogeneous solution or suspension. Surfactants include any complex capable of non-covalent interaction with the active pharmaceutical agent so as to facilitate dissolution or homogeneous suspension of the active pharmaceutical agent.

Pharmaceutical compositions including the active pharmaceutical agent may be prepared in a form that facilitates topical or transdermal administration. Such preparations may be in the form of a liquid solution, cream, paste, lotion, shake lotion, powder, emulsion, ointment, gel base, transdermal patch or iontophoresis device. Examples of bases used in such compositions include petrolatum, lanolin, polyethylene glycols, beeswax, mineral oil, diluents such as water and alcohol, and emulsifiers and stabilizers, thickening agents, or any other suitable base now known or yet to be disclosed.

Addition of a pharmaceutical composition to cancer cells includes all actions by which an effect of the pharmaceutical composition on the cancer cell is realized. The type of addition chosen will depend upon whether the cancer cells are in vivo, ex vivo, or in vitro, the physical or chemical properties of the pharmaceutical composition, and the effect the composition is to have on the cancer cell. Nonlimiting examples of addition include addition of a solution including the pharmaceutical composition to tissue culture media in which in vitro cancer cells are growing; any method by which a pharmaceutical composition may be administered to an animal including intravenous, per os, parenteral, or any other of the methods of administration; or the activation or inhibition of cells that in turn have effects on the cancer cells such as immune cells (e.g. macrophages and CD8+ T cells) or endothelial cells that may differentiate into blood vessel structures in the process of angiogenesis or vasculogenesis.

Determination of an effective amount of the active pharmaceutical agent is within the capability of those skilled in the art, especially in light of the detailed disclosure provided herein. The effective amount of a pharmaceutical composition used to affect a particular purpose as well as a pharmacologically acceptable dose determined by toxicity, excretion, and overall tolerance may be determined in cell cultures or experimental animals by pharmaceutical and toxicological procedures either known now by those skilled in the art or by any similar method yet to be disclosed. One example is the determination of the $IC_{50}$ (half maximal inhibitory concentration) of the pharmaceutical composition in vitro in cell lines or target molecules. Another example is the determination of the $LD_{50}$ (lethal dose causing death in 50% of the tested animals) of the pharmaceutical composition in experimental animals. The exact techniques used in determining an effective amount will depend on factors such as the type and physical/chemical properties of the pharmaceutical composition, the property being tested, and whether the test is to be performed in vitro or in vivo. The determination of an effective amount of a pharmaceutical composition will be well known to one of skill in the art who will use data obtained from any tests in making that determination. Determination of an effective amount of disclosed compound for addition to a cancer cell also includes the determination of an effective therapeutic amount, including the formulation of an effective dose range for use in vivo, including in humans.

Treatment is contemplated in living entities including but not limited to mammals (particularly humans) as well as other mammals of economic or social importance, including those of an endangered status. Further examples include livestock or other animals generally bred for human consumption and domesticated companion animals.

The toxicity and therapeutic efficacy of a pharmaceutical composition may be determined by standard pharmaceutical procedures in cell cultures or animals. Examples include the determination of the $IC_{50}$ and the $LD_{50}$ for a subject compound. The data obtained from these cell culture assays and animal studies can be used in formulating a range of dosage for use in human. The dosage may vary depending upon the dosage form employed and the route of administration utilized.

The effective amount of the pharmaceutical composition to result in the slowing of expansion of the cancer cells would preferably result in a concentration at or near the target tissue that is effective in slowing cellular expansion in cancer cells, but have minimal effects on non-cancer cells, including non-cancer cells exposed to radiation or recognized chemotherapeutic chemical agents. Concentrations that produce these effects can be determined using, for example, apoptosis markers such as the apoptotic index and/or caspase activities either in vitro or in vivo.

Treatment of a condition is the practice of any method, process, or procedure with the intent of halting, inhibiting, slowing or reversing the progression of a disease, disorder or condition, substantially ameliorating clinical symptoms of a disease disorder or condition, or substantially preventing the appearance of clinical symptoms of a disease, disorder or condition, up to and including returning the diseased entity to its condition prior to the development of the disease.

The addition of a therapeutically effective amount of the pharmaceutical composition encompasses any method of dosing of a composition. Dosing of the disclosed compound may include single or multiple administrations of any of a number of pharmaceutical compositions that include the disclosed compound as an active ingredient. Examples include a single administration of a slow release composition, a course of treatment involving several treatments on a regular or irregular basis, multiple administrations for a period of time until a diminution of the disease state is achieved, preventative treatments applied prior to the instigation of symptoms, or any other dosing regimen known in the art or yet to be disclosed that one skilled in the art would recognize as a potentially effective regimen. A final dosing regimen including the regularity of and mode of administration will be dependent on any of a number of factors including but not limited to the subject being treated; the severity of the affliction; the manner of administration, the stage of disease development, the presence of one or more other conditions such as pregnancy, infancy, or the presence of one or more additional diseases; or any other factor now known or yet to be disclosed that affects the choice of the mode of administration, the dose to be administered and the time period over which the dose is administered.

Pharmaceutical compositions that include the active pharmaceutical agent may be administered prior to, concurrently with, or after administration of a second pharmaceutical composition that may or may not include the active pharmaceutical agent. If the compositions are administered concurrently, they are administered within one minute of each other. If not administered concurrently, the second pharmaceutical composition may be administered a period of one or more minutes, hours, days, weeks, or months before or after the pharmaceutical composition that includes the compound Alternatively, a combination of pharmaceutical compositions may be cyclically administered. Cycling therapy involves the administration of one or more pharmaceutical compositions for a period of time, followed by the administration of one or more different pharmaceutical compositions for a period of time and repeating this sequential administration, in order to reduce the development of resistance to one or more of the compositions, to avoid or reduce the side effects of one or more of the compositions, and/or to improve the efficacy of the treatment.

The invention further encompasses kits that facilitate the administration of the pharmaceutical composition to a diseased entity. An example of such a kit includes one or more unit dosages of the active pharmaceutical agent. The unit dosage would be enclosed in a preferably sterile container and would be comprised of the disclosed compound and a pharmaceutically acceptable carrier. In another aspect, the unit dosage would comprise one or more lyophilates of the compound. In this aspect of the invention, the kit may include another preferably sterile container enclosing a solution capable of dissolving the lyophilate. However, such a solution need not be included in the kit and may be obtained separately from the lyophilate. In another aspect, the kit may include one or more devices used in administrating the unit dosages or a pharmaceutical composition to be used in combination with the compound. Examples of such devices include, but are not limited to, a syringe, a drip bag, a patch or an enema. In some aspects of the invention, the device comprises the container that encloses the unit dosage.

Pharmaceutical compositions including the active pharmaceutical agent may be used in methods of treating cancer. Such methods involve the administration of a therapeutic amount of a pharmaceutical composition that includes the active pharmaceutical agent and/or a pharmaceutically acceptable salt thereof to a mammal, preferably a mammal in which a cancer has been diagnosed.

A therapeutic amount further includes the prevention of progression of the cancer to a neoplastic, malignant or metastatic state. Such preventative use is indicated in conditions known or suspected of preceding progression to cancer, in particular, where non- or precancerous cell growth consisting of hyperplasia, metaplasia, or most particularly, dysplasia has occurred (for review of such abnormal growth conditions, see Robbins and Angell, 1976, *Basic Pathology*, 2d Ed., W. B. Saunders Co., Philadelphia, pp. 68-90, incorporated by reference). Hyperplasia is a form of controlled cell proliferation involving an increase in cell number in a tissue or organ, without significant alteration in structure or activity. For example, endometrial hyperplasia often precedes endometrial cancer and precancerous colon polyps often transform into cancerous lesions. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype or of a malignant phenotype, displayed in vivo or displayed in vitro by a cell sample derived from a patient can indicate the desirability of prophylactic/ therapeutic administration of the pharmaceutical composition that includes the compound. Such characteristics of a transformed phenotype include morphology changes, looser substratum attachment, loss of contact inhibition, loss of anchorage dependence, protease release, increased sugar transport, decreased serum requirement, expression of fetal antigens, disappearance of cell surface proteins, etc. Further examples include leukoplakia, featuring a benign-appearing hyperplastic or dysplastic lesion of the epithelium, or Bowen's disease, a carcinoma in situ. Both of theses are precancerous lesions indicative of the desirability of prophylactic intervention. In another example, fibrocystic disease including cystic hyperplasia, mammary dysplasia, adenosis, or benign epithelial hyperplasia is indicates desirability of prophylactic intervention.

In some aspects of the invention, use of the pharmaceutical composition may be determined by one or more physical factors such as tumor size and grade or one or more molecular markers and/or expression signatures that indicate prognosis and the likely response to treatment with the compound. For example, determination of estrogen (ER) and progesterone (PR) steroid hormone receptor status has become a routine procedure in assessment of breast cancer patients. See, for example, Fitzgibbons et al, Arch. Pathol. Lab. Med. 124:966-78, 2000, incorporated by reference. Tumors that are hormone receptor positive are more likely to respond to hormone therapy and also typically grow less aggressively, thereby resulting in a better prognosis for patients with ER+/PR+ tumors. In a further example, overexpression of human epidermal growth factor receptor 2 (HER-2/neu), a transmembrane tyrosine kinase receptor protein, has been correlated with poor breast cancer prognosis (see, e.g., Ross et al, The Oncologist 8:307-25, 2003), and Her-2 expression levels in breast tumors are used to predict response to the anti-Her-2 monoclonal antibody therapeutic trastuzumab (Herceptin®, Genentech, South San Francisco, Calif.).

In another aspect of the invention, the diseased entity exhibits one or more predisposing factors for malignancy that may be treated by administration of a pharmaceutical composition including the compound. Such predisposing factors include but are not limited to chromosomal translocations associated with a malignancy such as the Philadelphia chromosome for chronic myelogenous leukemia and t (14; 18) for follicular lymphoma; an incidence of polyposis or Gardner's syndrome that are indicative of colon cancer; benign monoclonal gammopathy which is indicative of multiple myeloma, kinship with persons who have had or currently have a cancer or precancerous disease, exposure to carcinogens, or any other predisposing factor that indicates in increased incidence of cancer now known or yet to be disclosed.

The invention further encompasses methods of treating cancer that comprise combination therapies that comprise the administration of a pharmaceutical composition including the disclosed compound and another treatment modality. Such treatment modalities include but are not limited to, radiotherapy, chemotherapy (e.g., conventional chemotherapy, including the use of compounds such as temozolomide), surgery, immunotherapy, cancer vaccines, radioimmunotherapy, treatment with pharmaceutical compositions other than those which include the disclosed compound, or any other method that effectively treats cancer in combination with the disclosed compound now known or yet to be disclosed. Combination therapies may act synergistically. That is, the combination of the two therapies is more effective than either therapy administered alone. This results in a situation in which lower dosages of both treatment modality may be used effectively. This in turn reduces the toxicity and side effects, if any, associated with the administration either modality without a reduction in efficacy.

In another aspect of the invention, the pharmaceutical composition including the disclosed compound is administered in combination with a therapeutically effective amount of radiotherapy. The radiotherapy may be administered concurrently with, prior to, or following the administration of the pharmaceutical composition including the compound. The radiotherapy may act additively or synergistically with the pharmaceutical composition including the compound. This particular aspect of the invention would be most effective in cancers known to be responsive to radiotherapy. Cancers known to be responsive to radiotherapy include, but are not limited to, Non-Hodgkin's lymphoma, Hodgkin's disease, Ewing's sarcoma, testicular cancer, prostate cancer, ovarian cancer, bladder cancer, larynx cancer, cervical cancer, nasopharynx cancer, breast cancer, colon cancer, pancreatic cancer, head and neck cancer, esophageal cancer, rectal cancer, small-cell lung cancer, non-small cell lung cancer, brain tumors, other CNS neoplasms, or any other such tumor now known or yet to be disclosed.

Examples of pharmaceutical compositions that may be used in combination with the active pharmaceutical agent(s) may include common chemotherapeutic agents/compositions such as cis-diamminedichloro platinum (II) (cisplatin), doxorubicin, 5-fluorouracil, taxol, and topoisomerase inhibitors such as etoposide, teniposide, irinotecan and topotecan. For example, the chemotherapeutic agents might also include TROY inhibitors, Pyk2 inhibitors, Rac1 inhibitors, Dock180 inhibitors, Dock7 inhibitors, temozolomide and bevacizumab. Still other pharmaceutical compositions include antiemetic compositions such as metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine and tropisetron.

Still other examples of pharmaceutical compositions that may be used in combination with the pharmaceutical composition including the disclosed compound are hematopoietic colony stimulating factors. Examples of hematopoietic colony stimulating factors include, but are not limited to, filgrastim, sargramostim, molgramostim and epoietin alfa. Alternatively, the pharmaceutical composition including the disclosed compound may be used in combination with an anxiolytic agent. Examples of anxiolytic agents include, but are not limited to, buspirone, and benzodiazepines such as diazepam, lorazepam, oxazapam, chlorazepate, clonazepam, chlordiazepoxide and alprazolam.

Pharmaceutical compositions that may be used in combination with pharmaceutical compositions that include the disclosed compound may include analgesic agents. Such agents may be opioid or non-opioid analgesic. Non-limiting examples of opioid analgesics include morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam, sulindac or any other analgesic now known or yet to be disclosed.

In other aspects of the invention, pharmaceutical compositions including the disclosed compound may be used in combination with a method that involves treatment of cancer ex vivo. One example of such a treatment is an autologous stem cell transplant. In this method, a diseased entity's autologous hematopoietic stem cells are harvested and purged of all cancer cells. A therapeutic amount of a pharmaceutical composition including the disclosed compound may then be administered to the patient prior to restoring the entity's bone marrow by addition of either the patient's own or donor stem cells.

Cancers that may be treated by pharmaceutical compositions including the disclosed compound either alone or in combination with another treatment modality include solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Additional cancers that may be treated by pharmaceutical compositions including the disclosed compound include blood borne cancers such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

Examples that represent different aspects of the invention follow. Such examples should not be construed as limiting the scope of the disclosure. Alternative mechanistic pathways and analogous structures within the scope of the invention would be apparent to those skilled in the art.

The invention encompasses inhibitors of cell migration activity and inhibitors of effector recruitment activity. Inhibition encompasses any action that hinders, from any detectable level up to and including complete inactivation, the progression of a biological process. Such biological processes include expression of a gene or activities of a gene product, progression of a disease, normal and abnormal metabolic activities, interactions between entities within an organism, or interactions between one organism and another. Further nonlimiting examples of biological processes include development, death, maturation, infection, pain, apoptosis, or homeostasis. Inhibition includes actions that silence or repress the expression of a gene. Inhibition also includes actions that hinder the activity of the RNA product, protein product, or postranslationally modified protein product of a gene. Inhibition may be effectuated through a single agent that inactivates a single gene or gene product, by a single agent that inactivates a combination of more than one gene or gene product, a combination of agents that inactivates a single gene or gene product or a combination of agents that inactivates a combination of more than one gene or gene product.

Inhibition may be effectuated directly by an agent that directly causes the inhibition of a biological process or by agents that trigger one or more different biological processes to effectuate the inhibition of the first biological process. Agents that cause inhibition may also be called inhibitors.

Examples of inhibitors include compositions such as compounds that trigger RNAi silencing such as microRNA or siRNA, small molecular compounds, proteins such as soluble receptors or antibodies or any fragment thereof, including an Fab, $F(ab)_2$, Fv, scFv, Fc, phage display antibody, peptibody or any other composition of matter that may inactivate or hinder a biological process. Further nonlimiting examples of inhibitors include X-rays, UV rays, visible light including laser light, and sound.

Cell migration activity includes any mode through which a cell may move in two-dimensional or three-dimensional space. Such migration includes movement through the use of pseudopodia including the adhesion of pseudopodia to a surface, a flagellum, a cilium, acts of amoeboid movement, extravasation, myosin-actin interactions, microtubule extension, or any other process through which a cell moves itself from one place to another or changes its morphology. In one aspect of the invention, cell migration activity is measured through cell adhesion. Using adhesion, cell migration activity may be measured by cell-cell aggregation, monolayer radial migration, including adhesion to a cell matrix comprising laminin, BSA or any other cell matrix component, three dimensional spheroid dispersion, or any other method that measures adhesion based cellular migration in space. Migration activity may be measured by any method that detects that a cell has moved from one place to another or has changed its morphology. Such methods include flow cytometry, capillary electrophoresis, visual examination by light, fluorescence, or electron microscopy, or any such method known in the art or yet to be developed. Inhibitors of cell migration activity are agents that disrupt any molecular or cellular process involved in cell migration activity.

Effector recruitment activity includes any activity of a protein that contributes to the formation of a complex of two or more molecules that serves to catalyze one or more chemical reactions. Effectors include any protein, nucleic acid or other molecule that may be included in a complex that performs one or more biological activities. Recruitment activity encompasses any protein-protein interaction including phosphorylation, dephosphorylation and other enzymatic activities, adhesion, signaling cascades, and cytokine/chemokine interactions, any protein-nucleic acid interactions, such as any of those involved in transcription, translation or DNA replication, or any other process that includes a protein interacting with another molecule. Inhibitors of effector recruitment activity may disrupt the interaction of a molecule with any of the proteins listed above, the interaction between any of those proteins with each other, and further includes any members of a complex that might be later identified.

In one aspect of the invention, inhibitors of effector recruitment activity may be identified on the basis of their ability to disrupt the binding of a molecule to one or more of its effectors. This specific binding may be measured by any method that allows the measurement of a protein-protein interaction known in the art. Such method include the following examples, alone or in combination as necessary: co-immunoprecipitation, biomolecular fluorescence complementation, fluorescence resonance energy transfer, label transfer, a yeast two-hybrid screen, in-vivo crosslinking, tandem affinity purification, chemical crosslinking, quantitative immunoprecipitation combined with knockdown (QUICK), dual polarization interferometry, protein-protein docking, static light scattering, immunoprecipitation plus mass-spectrometry, Strep-protein interaction experiment (SPINE), surface plasmon resonance, fluorescence correlation spectroscopy, or any other method of measuring the specific interaction between one protein and another now known in the art or yet to be disclosed.

In another aspect of the invention a glioblastoma patient is treated by first assessing the expression of a target and then treating with an effective dose of an inhibitor of that target, potentially in combination with Temozolomide. The effective dose of a compound is that amount effective to prevent occurrence of the symptoms of a disorder or to treat some symptoms of the disorder from which the patient suffers. Effective dose also includes an effective amount, a therapeutic amount, or any amount sufficient to elicit the desired pharmacological or therapeutic effects, thus resulting in effective prevention or treatment of the disorder. Thus, when treating a patient with glioblastoma, an effective amount of compound is an amount sufficient to slow, or arrest the progression, migration, metastasis, growth, or development of the tumor with the result that life is extended. Prevention includes a delay in onset of symptoms. Treatment includes a decrease in the symptoms associated with the disorder or an amelioration of the recurrence of the symptoms of the disorder. A pharmacologically acceptable dose encompasses any dose that may be administered to a patient that will not be lethal to the patient or cause effects that threaten the health or the life of the patient.

Patients include any human being, nonhuman primate, companion animal, or mammal suffering from a disease. In one aspect of the invention, the patient has symptoms that signify the presence of a tumor or other growth in the brain. Such symptoms include headache, seizures, mental or personality changes, mass effect, or one of a number of focal or localized systems including ringing or buzzing sounds, hearing loss, loss of coordination, reduced sensation, weakness or paralysis, difficulty with walking or speech, difficulty keeping balance, decreased muscle control, or double vision. Patients may display one or more different brain tumor types including acoustic neurinoma, astrocytoma, ependymoma, glioblastoma multiforme, meningioma, metastatic tumors originating from another tumor type, mixed glioblastoma, oligodendroglioblastoma, or pineal region tumor.

EXAMPLE

Elements and acts in the example are intended to illustrate the invention for the sake of simplicity and have not necessarily been rendered according to any particular sequence or embodiment. The example is also intended to establish possession of the invention by the Inventors.

Members of the TNFR superfamily (TNFRSF), most notably TNFR1, have been shown to play a role in inducing cell invasion and migration in several cancer types. An expression microarray database containing 195 clinically annotated brain tumor specimens publicly available at NCBI's Gene Expression Omnibus as dataset GSE4290 was analyzed. Snap-frozen specimens from epileptogenic foci (NB, n=24), low-grade astrocytomas (LGA, n=29), and glioblastoma multiforme (GBM, n=82) with clinical information were collected at the Hermelin Brain Tumor Center, Henry Ford Hospital (Detroit, Mich.) as previously described (See Reference 24). Gene expression profiling was conducted on all samples using Affymetrix U133 Plus 2 GeneChips according to the manufacturer's protocol at the Neuro-Oncology Branch at the National Cancer Institute (Bethesda, Md.). For the analysis, gene expression data were normalized in two ways: per chip normalization and per gene normalization across all samples in the collection. For per chip normalization, all expression data on a chip were normalized to the 50th percentile of all values on that chip. For per gene normalization, the data for a given gene were normalized to the median expression level of that gene across all samples. Gene expression differences were deemed statistically significant using parametric tests where variances were not assumed equal (Welch analysis of variance). Expression values were then filtered for highly variable (differentially expressed) genes (coefficient of variation>30%) across samples producing a list of 7322 genes. TROY/TNFRSF19 expression is significantly differentially expressed among brain specimens. In normal brain specimens, TROY expression is relatively low, but is increased with increasing tumor grade and is significantly higher in GBM samples (n=82) (See FIG. 1). Quantitative RT-PCR was performed on independent non-neoplastic (n=10), LGA (n=6), anaplastic astrocytoma (n=4), and GBM (n=22) specimens. Normal brain specimens show relatively low mRNA levels for TROY as compared to the brain tumor samples (p<0.01). In GBM specimens, the mRNA level of TROY is significantly higher than in normal brain (p<0.01) (See FIG. 2). Next, principal component analysis was done to discern possible relationships between subgroups of samples as in, for example, Reference 34. Kaplan-Meier survival curves were developed for each principal component cluster. One cluster had a median survival time of 401 days (short-term survival, ST) and the other cluster had a median survival time of 952 days (long-term survival, LT). Box-and-whisker plots for TROY expression level in each cluster derived from PC analysis were graphed. Significance between the two populations was tested with a two-sample t-test assuming unequal variances. Analysis of the Affymetrix expression values for TROY in the GBM specimens for each cluster showed that patients with GBM in the short-term survival cluster had higher expression of TROY (10.5) than GBM patients in the long term survival cluster (2.9; p<0.01) (See FIG. 3) This demonstrates that high TROY expression levels correlates with poor patient outcome while low TROY expression level corresponds with good patient outcome.

TROY is expressed in glioblastoma cell lines and siRNA-mediated depletion of TROY suppresses glioblastoma cell migration. The expression of TROY protein was assessed in four different cultured glioblastoma cell lines. The highest level of expression of TROY was seen in U118 cells, the next highest level of expression was seen in U87 cells, and the lowest level of expression was seen in T98G and SNB19 cells (See FIG. 4).

RNAi was used to suppress the expression of TROY in each of the four listed glioma cell lines and the migratory behavior of the cells on glioma-derived ECM was examined using a two-dimensional radial cell migration assay (See References 26 and 27). Suppression of TROY protein expression in all glioma cell lines was ~80-90% effective with each of two independent siRNA oligonucleotides. Representative results are shown for U118 cells (See FIG. 5). Further, suppression of TROY expression by siRNA resulted in a significant (p<0.05) inhibition of cell migration in all four cell lines (See FIG. 18).

T98G and SNB19 glioma cell lines that stably express of HA-epitope tagged TROY were produced through lentiviral transduction. These were used to further examine the role TROY signaling in glioma cell migration (See FIG. 7). Both the T98G and SNB19 lines normally express low levels of endogenous TROY. The cell lines with HA tagged-TROY showed a ~1.8-2.3-fold increase in cell migration rate (See FIG. 8). Migration of the HA-tagged TROY expressing cells was further tested in the context of an authentic brain microenvironment using an ex vivo organotypic rat brain slice model. T98G glioma cells that overexpressed TROY displayed a two-fold increase in the depth of cell invasion after 48 hours relative to controls (See FIG. 9). Immunolocalization of TROY using an anti-HA antibody revealed that TROY was localized near the cell perimeter and was enriched in lamellipodia (See FIG. 10B).

Potential effector molecules of TROY were found in immunoprecipitation experiments coupled with MALDI-TOF MS analysis. In one experiment, T98G cells expressing HA-tagged TROY and control T98G cells transfected with GFP were lysed, immunoprecipitated with anti-HA antibodies, and the immunoprecipitates resolved by SDS-PAGE. Prominent protein bands present in the immunoprecipitates of TROY expressing cells but absent in the immunoprecipitates of control cells of interest were recovered from the gel. Proteins were eluted, and trypsin-digested. MALDI-TOF and MS-MS analysis of the trypsin digests were performed on a Voyager reflector instrument (Applied Biosystems) and a Q-STAR mass spectrometer (Perceptive Biosystems) in positive ion mode.

The non-receptor protein tyrosine kinase Pyk2 was a candidate sequence identified by mass spectrometry in the TROY immunoprecipitate. Association of TROY with Pyk2 was verified by co-immunoprecipitation. T98G cells transfected with HA-tagged TROY or cotransfected with HA-tagged TROY and Pyk2 were immunoprecipitated with anti-HA antibodies and the precipitates immunoblotted with anti-Pyk2 antibodies (See FIG. 11). Both endogenous Pyk2 and transfected Pyk2 co-immunoprecipitated with TROY substantiating the intracellular interaction between TROY and Pyk2.

Depletion of Pyk2 expression by shRNA in TROY overexpressing T98G cells was performed to determine whether the association with Pyk2 was required for TROY-induced stimulation of glioma migration. Suppression of Pyk2 expression by shRNA significantly inhibited TROY stimulated glioma cell migration (See FIG. 12). Further, coexpression of a kinase inactive variant of Pyk2 (Pyk2KD) with TROY HA significantly inhibited the migration of the control T98G cells indicating that Pyk2 activity is required for TROY stimulated migration of glioma cells. (See FIG. 13). Finally, silencing of Pyk2 expression also inhibited TROY mediated Rac1 activation (See FIG. 15). Together, these results indicate that TROY-mediated glioma cell migration is dependent upon Pyk2 activity.

Rho GTPase family members, particularly Rac1 (See References 22-24, 28) effect the invasive behavior of glioblastoma cells. As a result, if TROY signaling influences Rac1 activity, then TROY is a marker of invasive glioblastoma and Rac1 is an effector molecule of TROY. U118 cells express a high endogenous level of TROY protein expression (See FIG. 4) and display high Rac1 activity (See FIG. 14). Reduction of TROY expression in U118 cells by siRNA resulted in decreased activity of Rac1 (See FIG. 14). Further, siRNA mediated reduction of TROY expression induced RhoA activation, showing that TROY signaling modulates Rac1 and RhoA GTPases activity in opposite directions. Indeed, it has been previously noted that in certain cell types, overexpression of TROY increased RhoA activation (See References 6 and 9) suggesting that TROY signaling may be modulated by cell type specific elements. To validate the effect of TROY on Rac1 activity, the activation of Rac1 in glioma cells overexpressing TROY was compared to the activation of Rac1 in untransfected cells. Overexpression of TROY resulted in a ~2-fold induction of Rac1 activation relative to untransfected cells (See FIG. 15).

Since Pyk2 interacts with TROY and mediates TROY-induced migration, the effect of Rac1 activation induced by TROY expression is dependent upon Pyk2 activity was determined. shRNA-mediated depletion of Pyk2 in TROY overexpressing glioma cells suppressed TROY induced Rac1 activity to the level of that in control cells. (See FIG. 15). This indicates that the TROY-mediated regulation of Rac1 activation is dependent upon Pyk2. Further, Rac1 expression in T98G cells overexpressing the TROY receptor was reduced by Rac1 siRNA. That reduction in Rac1 expression in was ~90% effective in T98G cells and caused a significant inhibition of TROY-mediated cell migration. (See FIG. 16).

A recent study suggest that TROY is activated by the TNF family ligand lymphotoxin-α to induce NFκB activation, whereas previous studies have not revealed specific interactions between TROY and any of the TNF family members (See Reference 29). Since Rac1 can influence multiple downstream signaling pathways, immunoblot analysis of lysates from TROY overexpressing cells were analyzed for detection of various signaling pathways and compared to lysates from untransfected cells. Increased phosphorylation of Akt, IκBα, and ERK1/2 in TROY overexpressing cells was observed relative to untransfected cells (See FIG. 18).

Activation of Akt and NFκB signaling pathways plays a critical role in cell survival. The effect of TROY expression on chemotherapy-induced apoptosis in glioma cells was then determined by comparing the sensitivity of control U118 glioma cells and U118 glioma cells reduced TROY expression by transfection of TROY specific RNAi to temozolomide treatment. U118 cells with reduced expression of TROY were significantly more sensitive to cell death following temozolomide treatment relative to U118 cells transfected with a negative RNAi control (See FIG. 19). Conversely, T98G glioma cells overexpressing TROY were significantly more resistant to temozolomide induced apoptosis relative to control transfected T98G glioma cells (See FIG. 20). Together, these data indicate that TROY stimulated glioma cell migration/invasion increases resistance to chemotherapy-induced cell death in glioma.

A number of RhoGTPases, including Rac1 Rac3 and Cdc42 (See References 22-25), contribute to glioblastoma cell invasion in vitro. The Rho GTPases are activated by GEFs. There are currently 80 RhoGEFs in the human genome. Of these GEFs, 26 are known Rac1 activators, and currently, it is not known which Rac GEFs contribute to Rac1 activity in glial tumors. Rac GEFs that mediate glioma invasion were identified by first mining the NCBI expression microarray database of human brain tumor specimens for the 26 GEFs known to have Rac exchange factor activity. Of the 26 GEFs, Ect2, Trio and Vav3 exhibited increased expression in glioblastomas (GBMs) versus normal brain. Depletion of Ect2, Trio, and Vav3 expression reduced Rac1 activity in glioblastoma cells which in turn led to a subsequent inhibition of glioblastoma cell migration and invasion. A library of small interfering RNAs (siRNAs) directed against all 26 Rac GEFs in the human genome was used to evaluate the role of RacGEF's in inhibiting glioma invasion in a 96-well format invasion assay. Two additional Rac GEFs—Dock180 and Dock7—were found to contribute to glioma invasion. Knockdown of Dock180 or Dock7 expression by RNAi significantly reduced glioma invasion in vitro (See FIG. 21). Dock180 has recently been reported (See Reference 30) to be overexpressed in invasive glioma cells where it regulates Rac1 activity and glioma cell invasion. To further examine the role of Dock7 in glioblastoma cell invasion using RNAi sequences that inhibit Dock 7 expression to inhibit the migration of SNB19 cells into rat brain slices, a well-established ex vivo organotypic model for glioma invasion. Knockdown of Dock7 expression significantly inhibited invasion relative to control cells (See FIG. 22).

Figure 23:
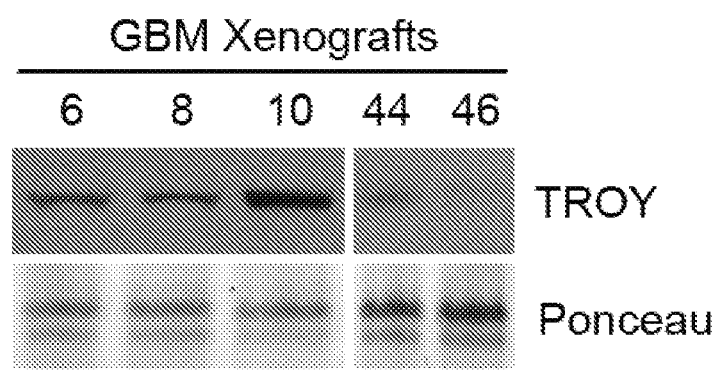
FIG. 23 depicts a Western blot showing TROY expression in glioblastoma xenografts grown in murine brain.

A significant limitation of the use of long-term established human glioma cell lines for orthotopic xenografts is their propensity to form discrete, non-invasive tumors with well circumscribed borders that push into the adjacent normal brain tissue (See References 31-33). This is in contrast to the diffuse highly infiltrative growth that defines primary GBM in patients. More important is the loss of genetic features and signatures in long-term established cell lines which are common to primary GBM. A model based on utilizing primary glioma xenografts established and maintained by direct heterotypic transplantation, propagation, and passaging of patient tumor surgical samples in immune deficient mice has been established. Intracranial tumors established with these GBM xenografts retain key histopathological characteristics of the aggressive behavior of the patients' tumors including local invasion at the tumor periphery and invasion along white matter tracks, as well as manifesting key genetic features such as preservation of EGFR amplification status. Therefore, tumors that arise from these xenograft lines adequately model primary GBM in patients (See References 34-36). TROY protein expression was examined in lysates obtained from 19 xenografts grown orthotopically in murine brain. Examination of TROY expression on the xenograft lysates showed a range of TROY expression. Representative immunoblots showing GBM xenografts with high TROY expression (GBM10), intermediate levels of TROY expression (GBM6, GBM8), or low levels of TROY expression (GBM44, GBM46) are shown in FIG. 23.

Figure 2:
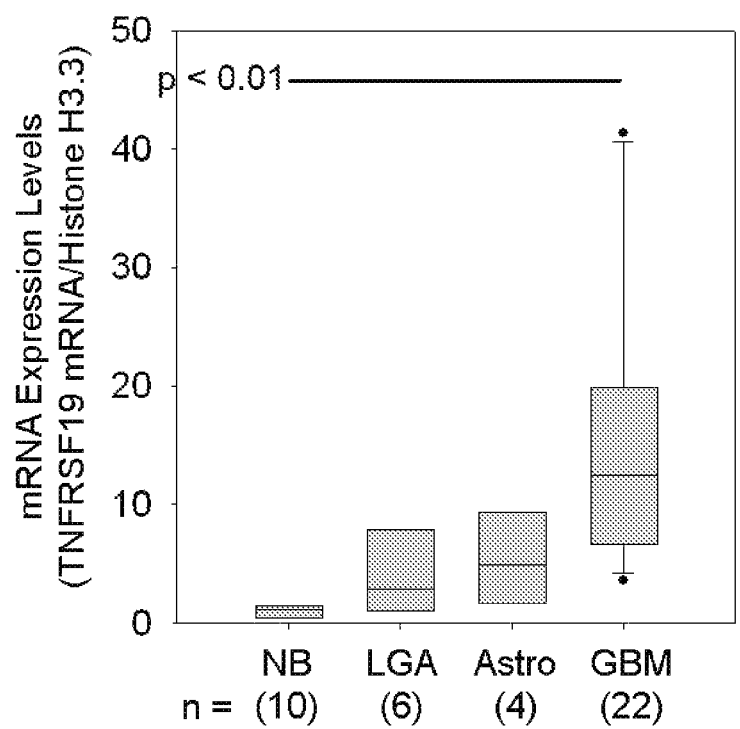
FIG. 2 depicts expression of TROY in a separate set of normal brain and various glioblastoma types by QRT-PCR.
Figure 3:
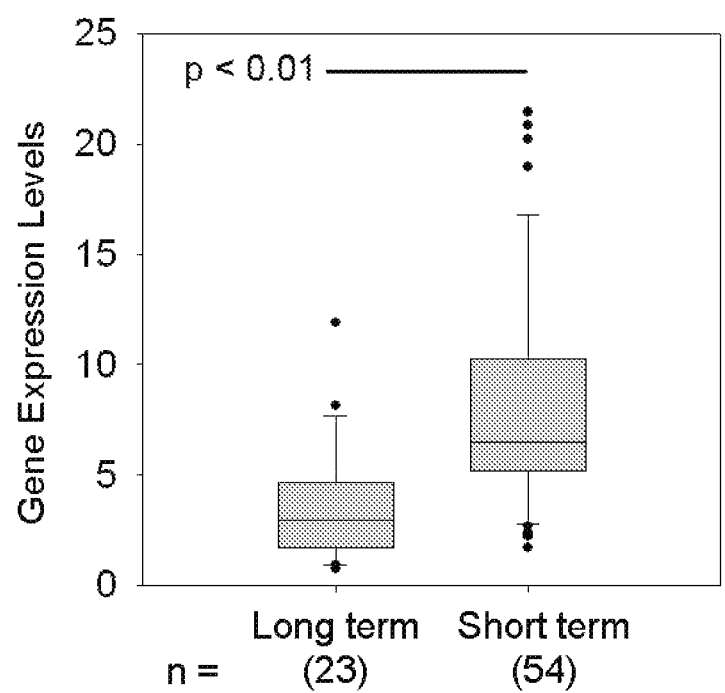
FIG. 3 depicts TROY expression data from the NCBI Gene Expression Omnibus GDS1962 dataset with tissues grouped as long-term and short-term survivors.

Referring now to FIG. 1: TROY mRNA expression levels derived from the NCBI Gene Expression Omnibus GDS1962 dataset are presented as box-and-whisker plots. The box for each gene indicates the interquartile range (25-75th percentile) and the line within this box indicates the median value. Bottom and top bars of the whisker indicate the 10th and 90th percentiles, respectively. Outliers are represented by closed circles. Significance between the indicated classes of brain specimens was tested using a two-sample t test assuming unequal variances. (NB=non-neoplastic brain; OL, Oligodendrogliomas; Astro=low grade astrocytomas; GBM=glioblastoma multiforme). Referring now to FIG. 2 Quantitative real-time PCR analysis of TROY expression in non-neoplastic brain (NB), grade 1 low grade astrocytoma (LGA), grade 2-3 Astrocytomas (Astro) and glioblastoma multiforme (GBM) indicates that a higher level of TROY expression signifies increased tumor grade. Values were normalized to histone H3.3 and HPRT1 reference genes. Data are presented as box-and-whisker plots. Referring now to FIG. 3: principal component analysis of brain tumors from NCBI Gene Expression Omnibus GDS1962 dataset revealed two groups differing by their survival and were denoted as long term (LT) survival and short-term (ST) survival. These indicate that a higher level of TROY expression signifies an association with short-term survival. Box-and-whisker plots for TROY expression in GBM specimens for each cluster are shown. Significance between the two populations was tested with a two-sample t test assuming unequal variances.

Figure 4:
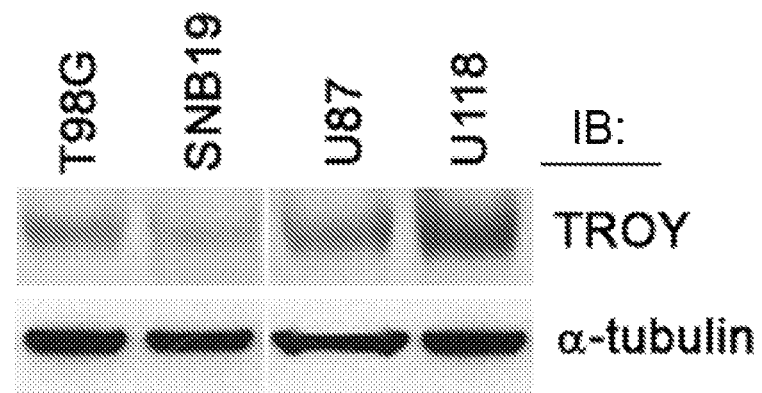
FIG. 4 depicts a Western blot showing expression of TROY in four glioblastoma cell lines.
Figure 5:
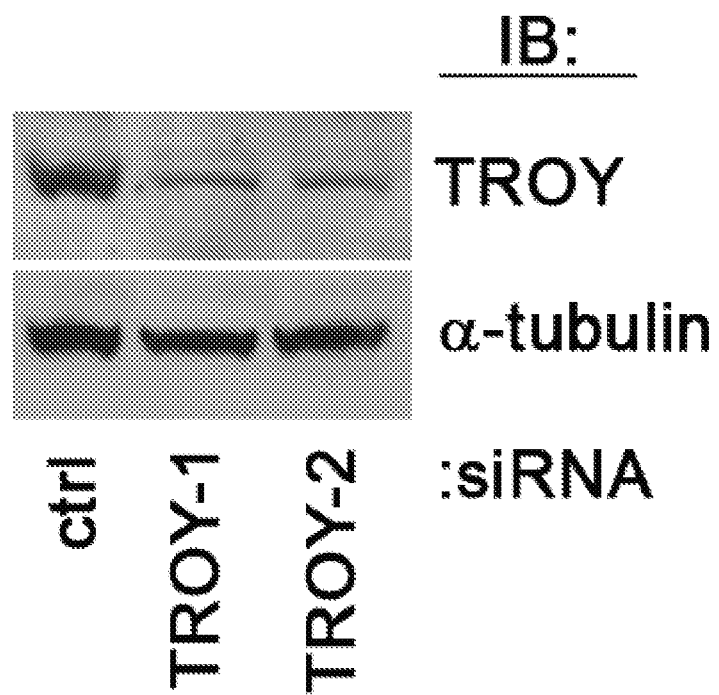
FIG. 5 depicts a Western blot showing suppression of TROY expression in two of the cell types using siRNA targeting TROY.
Figure 6:
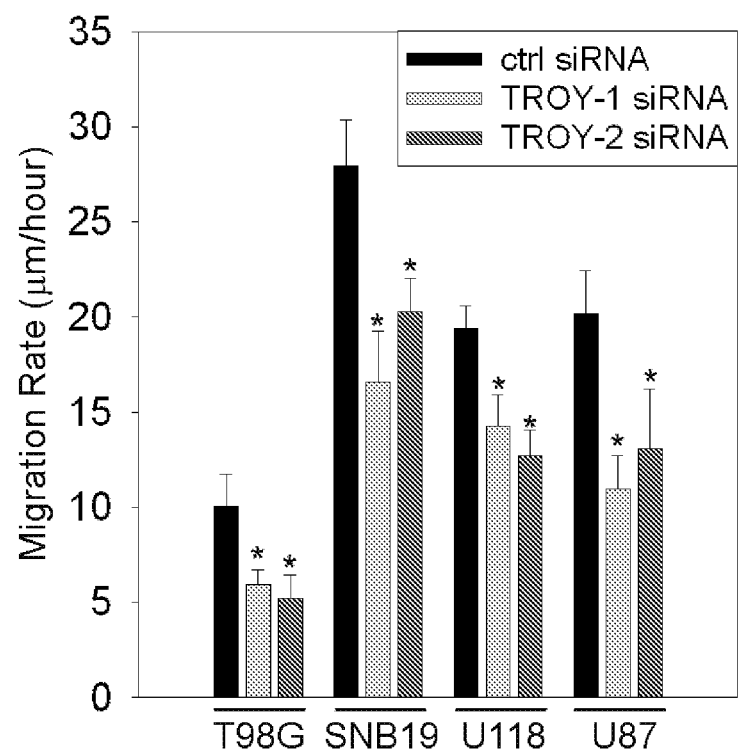
FIG. 6 depicts a graph showing significantly slowed migration of four glioblastoma cell lines when those lines are transfected with siRNA targeting TROY.
Figure 18:
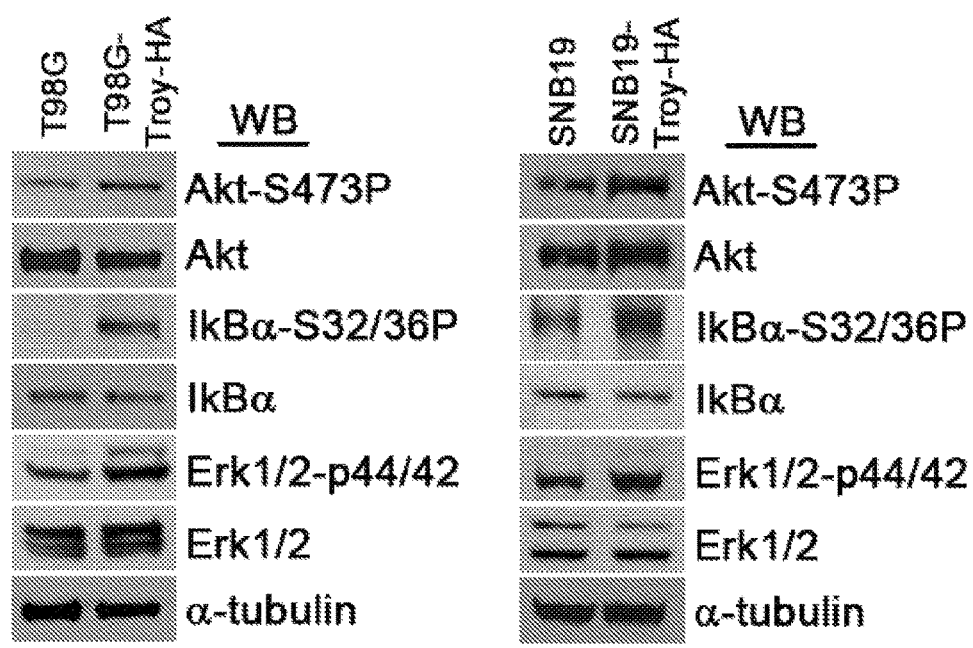
FIG. 18 depicts increased Akt, IkBa, and Erk1/2 phosphorylation when a glioblastoma cell line is transfected with HA-tagged TROY.

Referring now to FIG. 4: T98G, SNB19, U87, and U118 cell lysates were analyzed for endogenous level of TROY expression by immunoblotting. All express TROY with U87 and U118 cells having the highest expression level. The levels of α-tubulin protein were also immunoblotted to ensure equal sample loading. Referring now to FIG. 5: knockdown of TROY expression in U118 cells by two independent siRNA oligonucleotides. Note reduced expression of TROY protein in TROY-1 and TROY-2 transfected U118 cells. Referring now to FIG. 18: the migration rate of each of the four cell lines was slowed when the cell lines were transfected with siRNA oligonucleotides targeting TROY. siRNA targeting luciferase was used as a negative control. Migration rate was determined after 24 h migration on glioma derived ECM (*-$p<0.05$).

Figure 7:
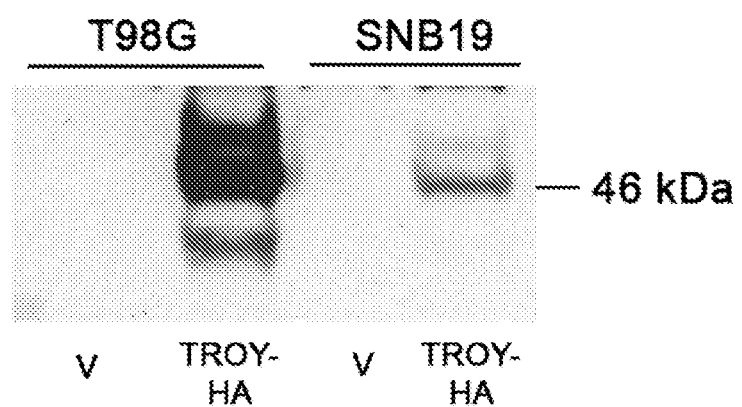
FIG. 7 depicts expression of a construct comprising HA-tagged TROY transfected into two glioblastoma cell lines.
Figure 8:
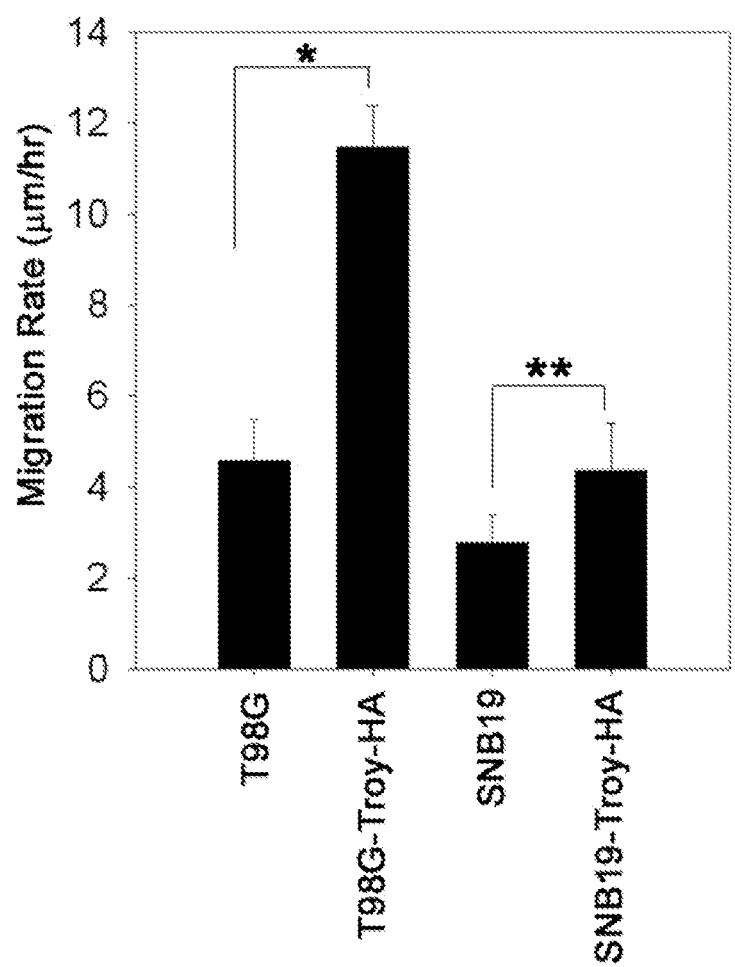
FIG. 8 depicts increased migration rate of cell lines transfected with the HA-tagged TROY construct.
Figure 9:
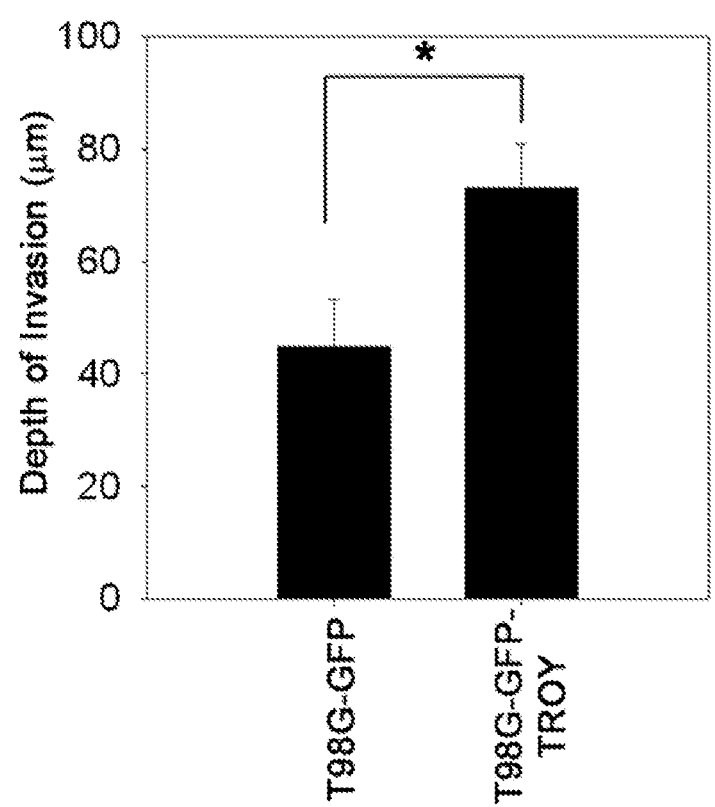
FIG. 9 depicts increased depth of invasion into rat brain slices by a GFP-tagged TROY transfected cell line.
Figures 10A, 10B, 10C:
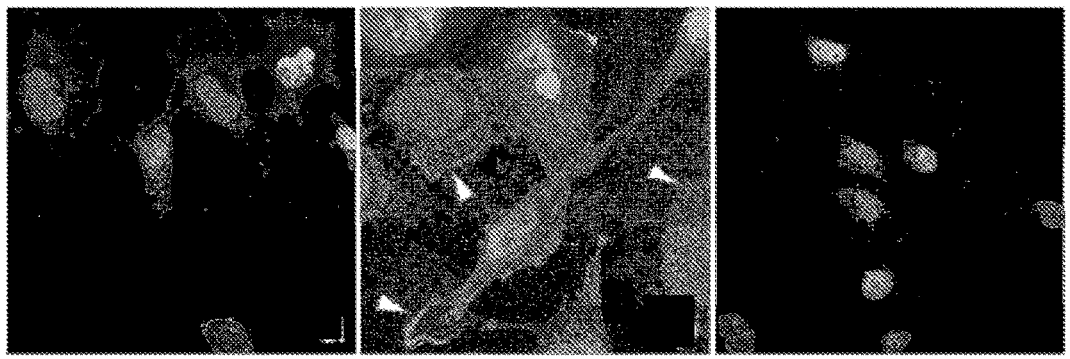
FIGS. 10A-10C depict immunofluorescent staining for HA in HA-tagged TROY transfected cell lines.

Referring now to FIG. 7: Lysates of T98G or SNB19 cells transduced with empty lentiviral vector (v) or lentiviral vector encoding HA-epitope tagged TROY immunoblotted with anti-HA antibody shows that TROY is overexpressed in cell lines transfected with the TROY construct. Referring now to FIG. 8: the migration rate of HA-TROY expressing glioma cells is faster than that of cells transduced with a negative control construct. Cell migration was assessed over 48 h. Data represents the average of three independent experiments (*, $p<0.01$; **, $p<0.05$). Referring now to FIG. 9: T98G cells stably expressing green fluorescent protein were transduced with lentiviruses expressing HA-tagged TROY. Cells were implanted into the bilateral putamen of rat organotypic brain slices and observed at 48 h. Depth of invasion was calculated from Z-axis images collected by confocal laser scanning microscopy. The mean value of the depth of invasion was obtained from six independent experiments (*, $p<0.01$). Cell lines transduced with a construct containing TROY displayed significantly greater depth of invasion. Referring now to FIGS. 10A, 10B, and 10C: immunofluorescent staining for Troy in T98G-Troy-HA cells using an anti-HA antibody shows that TROY localizes at the membrane periphery and within cellular extensions.

Figure 11:
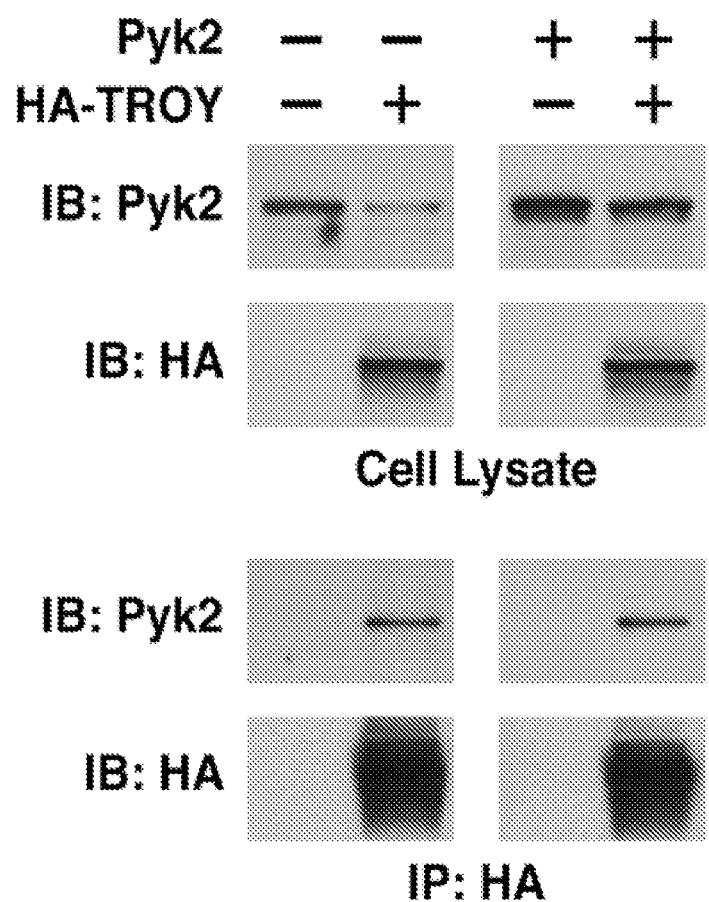
FIG. 11 depicts (top) a Western Blot showing cell lysates from a glioblastoma cell line transfected with Pyk2 or HA-tagged TROY as indicated and (bottom) a Western blot of immunoprecipitates with anti-HA antibodies that show an association of Pyk2 with TROY.
Figure 12:
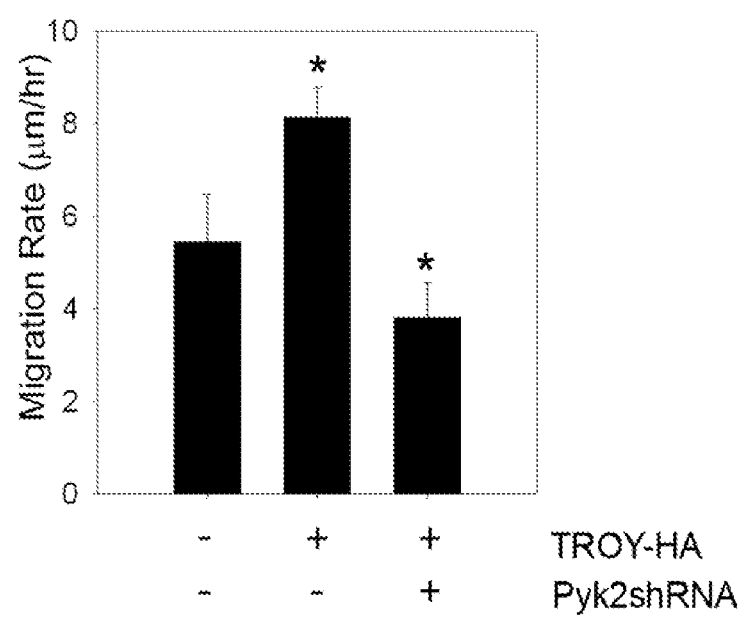
FIG. 12 depicts increased migration rate in a glioblastoma cell line transfected with HA-tagged TROY that is slowed when Pyk2 expression is suppressed.
Figure 13:
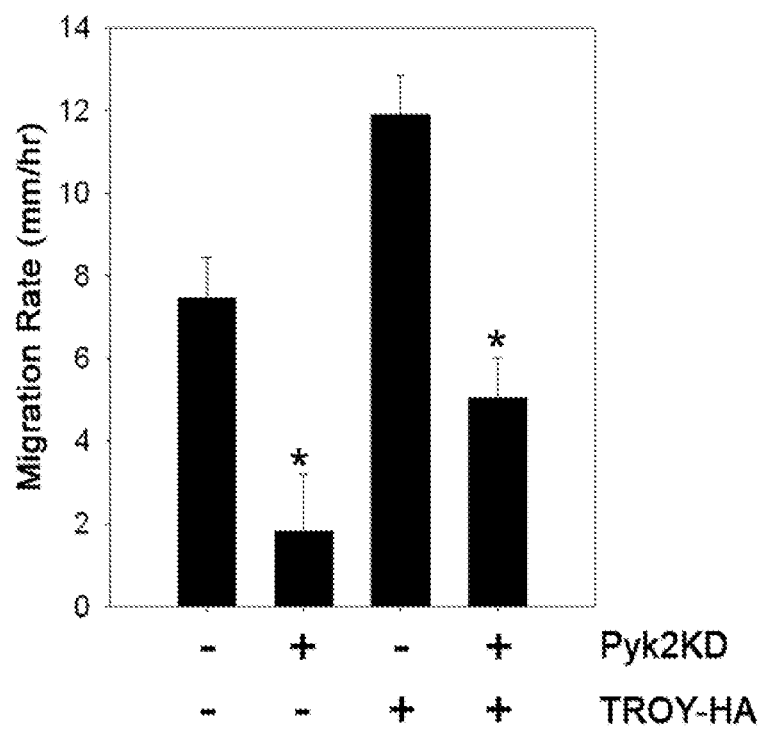
FIG. 13 depicts reduced migration rate in a glioblastoma cell line transfected with a dominant-negative Pyk2 construct, whether or not the TROY expression is endogenous or from HA-tagged TROY.

Referring now to FIG. 11: The top panel indicates that lysates of negative control transfected T98G cells, T98G cells transfected with HA-TROY, T98G cells transfected with Pyk2, or T98G cells cotransfected with HA-TROY and Pyk2 show expression of the transfected constructs when immunoblotted with anti-Pyk2 or anti-HA antibodies. In the bottom panel, the same cell lines were immunoprecipitated with anti-HA antibody and the precipitates immunoblotted with anti-HA or anti-Pyk2 indicating that Pyk2 associates with TROY. Referring now to FIG. 12: The inhibition of Pyk2 expression by RNAi targeting Pyk2 suppresses Troy-induced glioma migration. Migration rate of T98G, T98G-Troy-HA, and T98G-Troy-HA cells transfected with a shRNA targeting Pyk2 was assessed over 24 h using a radial migration assay on 10 µg/ml laminin substrate (*, $p<0.01$). T98G cells overexpressing TROY migrate at a faster rate than T98G cells that lack the TROY expressing construct. This effect is negatived by transfection with Pyk2-specific shRNA. Referring now to FIG. 13: inhibition of Pyk2 activity inhibits Troy-induced glioma migration. T98G or T98G-Troy-HA expressing cells were infected with recombinant adenoviruses expressing a Pyk2 variant lacking the Pyk2 kinase domain. (Pyk2KD). Cell migration was assessed over 24 h using a radial migration assay on 10 µg/ml laminin substrate (*, $p<0.01$). Transfection of the Pyk2KD construct into T98G cells that do not overexpress TROY slowed the migration rate of those cells. T98G cells overexpressing TROY migrate at an even faster rate, but this effect is mitigated by transfection with Pyk2KD.

Figure 14:
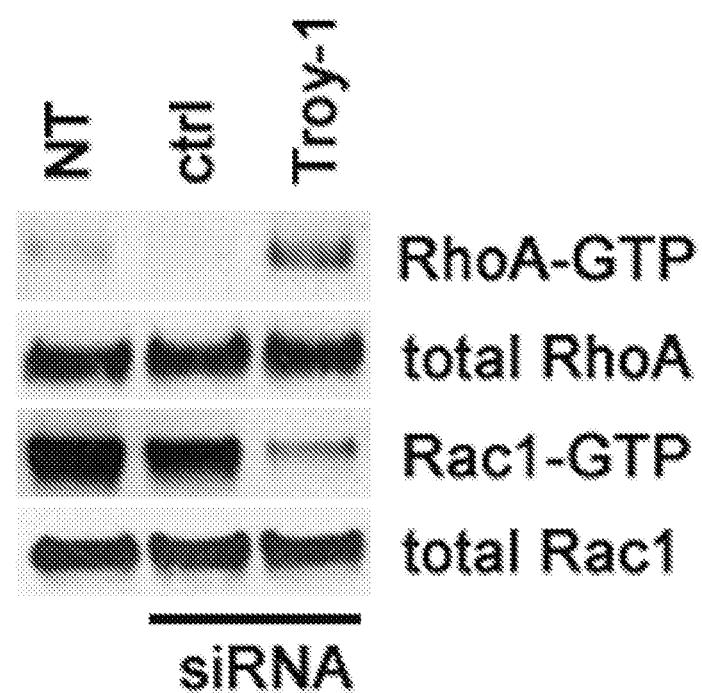
FIG. 14 depicts a Western blot showing increased phosphorylation of RhoA when TROY expression is suppressed and reduced phosphorylation of Rac-1 when TROY expression is suppressed.
Figure 15:
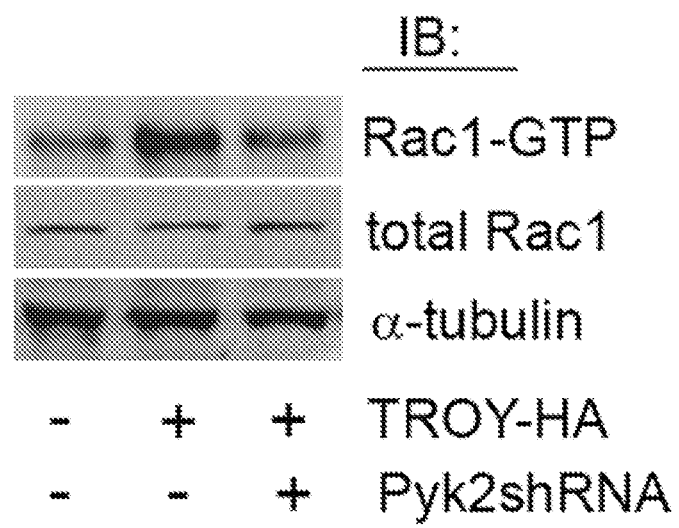
FIG. 15 depicts a Western blot showing increased phosphorylation of Rac-1 when a cell line is transfected with HA-tagged TROY. This effect is reduced when Pyk2 expression is suppressed.
Figure 16:
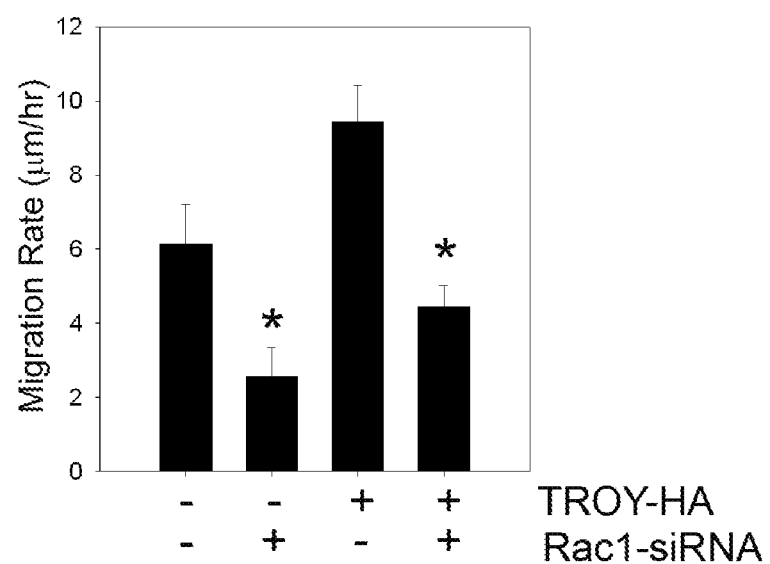
FIG. 16 depicts reduced migration of a glioblastoma cell line when Rac-1 expression is suppressed—whether or not the cell line expresses endogenous or HA-tagged TROY.
Figure 17:
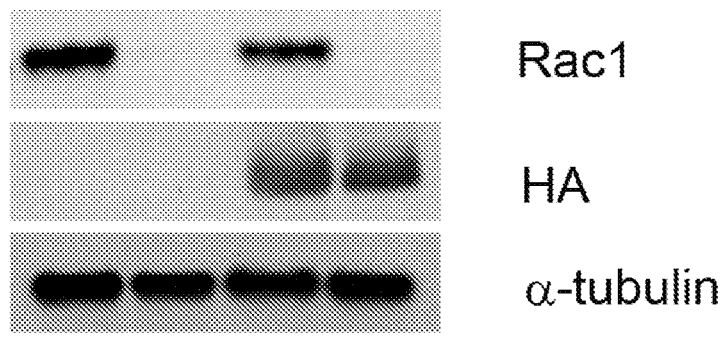
FIG. 17 depicts a Western blot validation of suppression of Rac1 expression by Rac1 siRNA using alpha tubulin as a loading control.

Referring now to FIG. 14: U118 cells were left untransfected (NT), transfected with an siRNA targeting nonmammalian luciferase (ctrl), or an siRNA targeting TROY (Troy-1). Cells were cultured under serum-free medium for an additional 16 hr prior to RhoA and Rac1 activation assays. Immunoblots show that RhoA is more likely to be phosphorylated and Rac-1 is dephosphorylated upon suppression of TROY1 expression. Referring now to FIG. 15: T98G and T98G-Troy-HA cells were transfected with a shRNA targeting Pyk2 and cultured under serum-free medium for 16 h. Lysates were then analyzed for activation of Rac1. Overexpression of TROY leads to more Rac1 phosphorylation. This effect is diminished when Pyk2 expression is suppressed. Referring now to FIG. 16: suppression of Rac1 expression by siRNA suppresses Troy-induced glioma cell migration. T98G and T98G-TROY-HA cells were transfected with an siRNA oligonucleotide targeting Rac1. Cell migration was assessed over 24 h using a radial migration assay on 10 mg/ml laminin substrate (*, $p<0.01$). Suppression of Rac1 expression reduced the migration rate of the cells indicating that TROY-1 mediated migration works through Rac1. Referring now to FIG. 17: a Western blot validating suppression of Rac1 and HA-TROY expression was performed.

Referring now to FIG. 18: TROY overexpression induces activation of Akt, NFkB and Erk1/2 signaling pathways. Cellular lysates of T98G glioma cells or T98G cells overexpressing TROY (left panel) and SNB19 glioma cells or SNB19 cells overexpressing TROY (right panel) were immunoblotted with the indicated antibodies. Equal sample loading was verified by immunoblotting lysates with an anti-α-tubulin antibody. Western blots indicate phosphorylation of Akt, IκBα, and Erk1/2.

Figure 19:
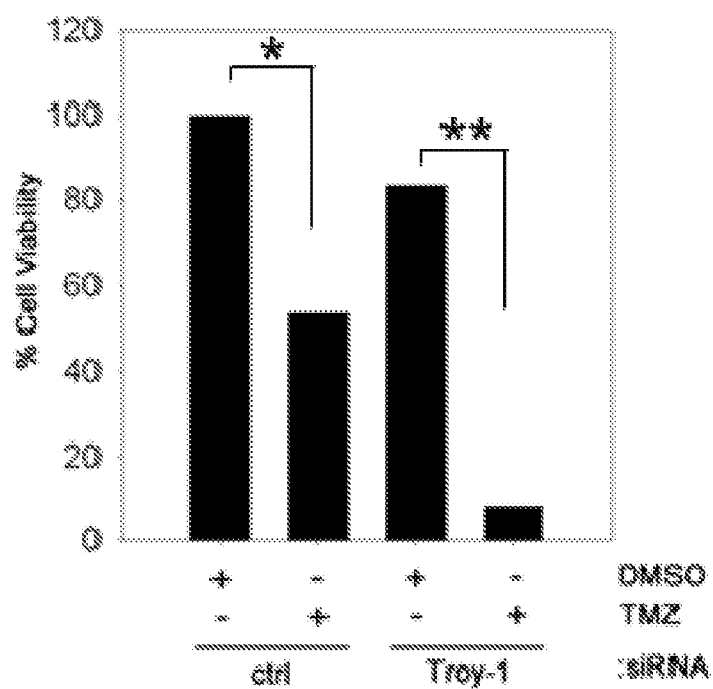
FIG. 19 depicts increased sensitivity of a glioblastoma cell line to temozolomide when TROY expression is suppressed.
Figure 20:
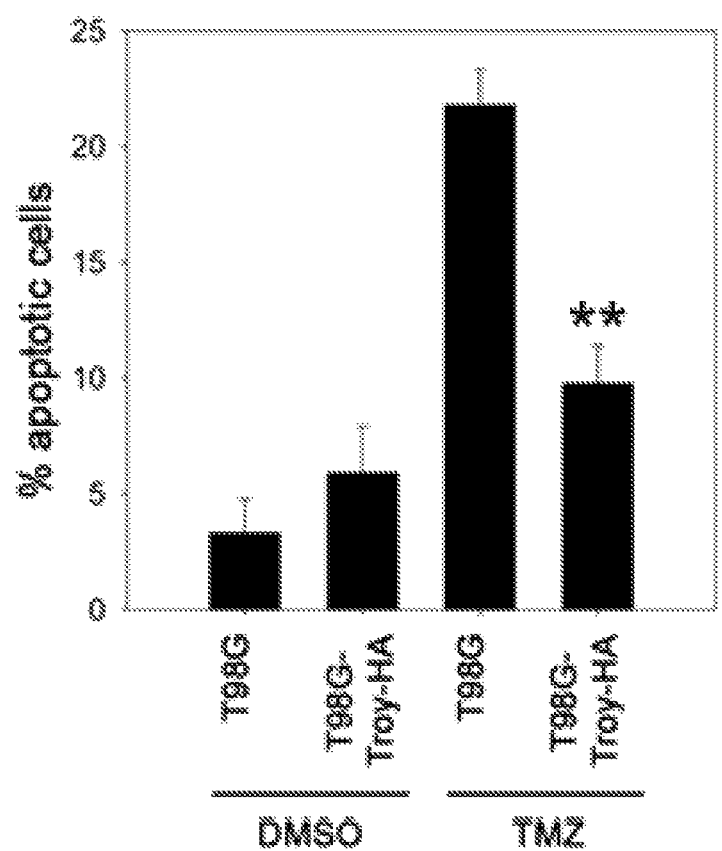
FIG. 20 depicts reduced sensitivity of a glioblastoma cell line to temozolomide when the cell line is transfected with an HA-tagged TROY construct.

Referring now to FIG. 19: U118 cells were transfected with a siRNA targeting TROY (Troy-1) or a siRNA targeting a nonmammalian gene. Cells were then treated with 250 μM of temozolomide (TMZ) or vehicle (DMSO) for 48 h. The percentage of cell viability was measured by Alamar Blue assay and normalized to the control siRNA untreated with TMZ (*, $p<0.01$; , $p<0.001$). The results indicate that when TROY expression is suppressed, the cells are rendered sensitive to temozolomide. Referring now to FIG. 20: T98G and T98G expressing TROY-HA were treated with 250 μM of TMZ or vehicle (DMSO) for 48 h. The percentage of cellular apoptosis was measured by annexin V staining followed by flow cytometry. Data represents the mean and S.D. from three independent experiments with each experiment conducted in triplicate (, $p<0.001$). The results show that overexpression of TROY decreases the number of cells that apoptose upon treatment with temozolomide and that overexpression of TROY increases resistance to temozolomide.

Figure 21:
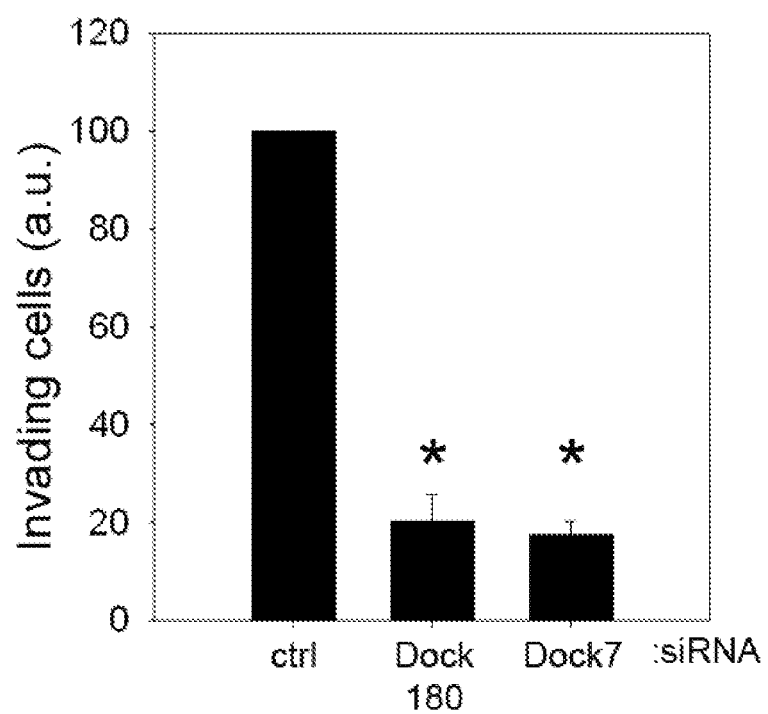
FIG. 21 depicts reduced migration of a glioblastoma cell line when Dock180 and Dock7 expression are suppressed.
Figure 22:
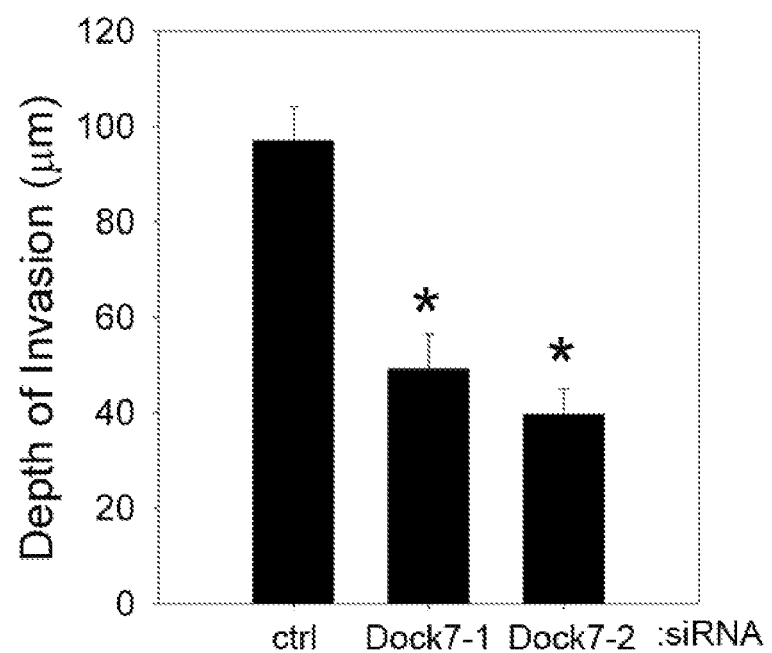
FIG. 22 depicts reduced depth of invasion of glioblastoma cells when Dock7 expression is suppressed using two different siRNAs.

Five known Rac1 activators were assessed for their ability to contribute to glioma invasion identified in a focused RhoGEF genome-wide siRNA screening approach. Referring now to FIG. 21: SNB19 cells transfected with siRNAs targeting luciferase (ctrl), Dock180, or Dock7 were plated in transwell invasion chambers coated with Matrigel, and 24 h later, cells that had migrated through the filter were stained and counted. Shown are the mean of at least two independent experiments; bars, ±SE (*, $p<0.001$). Results indicate that Dock180 and Dock7 are implicated in the invasive phenotype of glioma cells. Referring now to FIG. 22: SNB19-GFP cells were transfected with a siRNA targeting luciferase (ctrl) or two independent siRNAs targeting Dock7. After 24 h, cells were implanted into the bilateral putamen on rat organotypic brain slices and cultured for 48 h. Depth of invasion was calculated from Z-axis images collected by confocal laser scanning microscopy. The mean value of the depth of invasion (+/−SEM) was obtained from three independent experiments, performed in triplicates (*, $p<0.01$). The results further indicate a role of Dock7 in the development of an invasive phenotype.

Referring now to FIG. 23: Total cellular lysates from glioblastoma multiforme xenografts grown in murine brain orthopically were collected and immunoblotted for human TROY. Ponceau staining was used as a loading control.

The following methodologies were used according to some embodiments of the invention and in conjunction with the experiments further detailed herein.

Cell Culture Conditions: Human glioma cell line T98G (ATCC) was maintained in DMEM with high glucose (Invitrogen) supplemented with 10% heat-inactivated fetal bovine serum (FBS) (Invitrogen) in a 37° C., 5% $CO_2$ atmosphere at constant humidity. The primary glioma patient derived xenograft (PDX) lines GBM10 and GBM43 were derived from patient surgical samples and maintained as flank xenografts in immunodeficient mice. GBM10 and GBM43 flank tumor were resected, brought to single cell suspension via mechanical dissociation, and maintained in DMEM+10% FBS for in vitro experiments. In the experiments with FBS stimulation, the cells were serum starved (DMEM+0.1% Bovine Serum Albumin (BSA)) for 16 hours before stimulation with 10% FBS in DMEM.

Antibodies and Reagents: PPF, TMZ, and laminin were purchased from Sigma-Aldrich. Antibody against TROY was obtained from Abcam®. Antibodies against EGFR, TNFR1, Fn14, phospho-NF-κB, NF-κB, phospho-AKT, AKT, Cleaved PARP, α-Tubulin, and β-Actin were purchased from Cell Signaling Technology.

Referring now to FIGS. 24A, 24B, 24C, and 24D: The inventors investigated if PPF could be utilized pharmacologically to decrease TROY expression in GBM cells. The long-term established cell line T98G was first utilized to test the efficacy of PPF. Cells were treated with increasing concentration of PPF, 1 to 20 μM, lysed, and TROY expression assessed by immunoblotting. Briefly, monolayers of cells were washed in phosphate-buffered saline (PBS) containing 1 mM phenylmethylsulfonylfluoride and 1 mM sodium orthovanadate and then lysed in 2×SDS sample buffer containing protease and phosphatase inhibitors. Protein concentrations were determined using the BCA Assay (Pierce). Thirty micrograms of total protein was loaded per lane and separated by SDS-PAGE. After transfer, the nitrocellulose membrane (Invitrogen) was blocked with either 5% nonfat-milk or 5% BSA in TBST before addition of primary antibodies and followed with peroxidase-conjugated secondary antibody (Promega). Protein bands were detected using SuperSignal Chemiluminescent Substrate (Pierce) with a UVP BioSpectrum 500 Imaging System. TROY expression decreased in concentration dependent manner, with significant suppression observed even at 1 μM PPF concentration (FIG. 24A). The inventors further validated these findings in patient-derived primary cell lines GBM10 and GBM43, which overexpress TROY, and showed that 5 μM PPF concentration was effective in lowering TROY expression in all glioma cells lines (FIG. 24B). TROY expression also decreased in a time-dependent manner, when treated with 5 μM PPF for varying lengths of time, in both GBM10 and GBM43 cells (FIG. 24C). PPF specifically decreased TROY expression in these glioma cells lines and did not affect the expression of other cell surface receptors, including the related TNFR1 or EGFR (FIG. 24D). This data demonstrates that PPF decreases TROY expression in GBM cells in vitro.

Figure 25A:
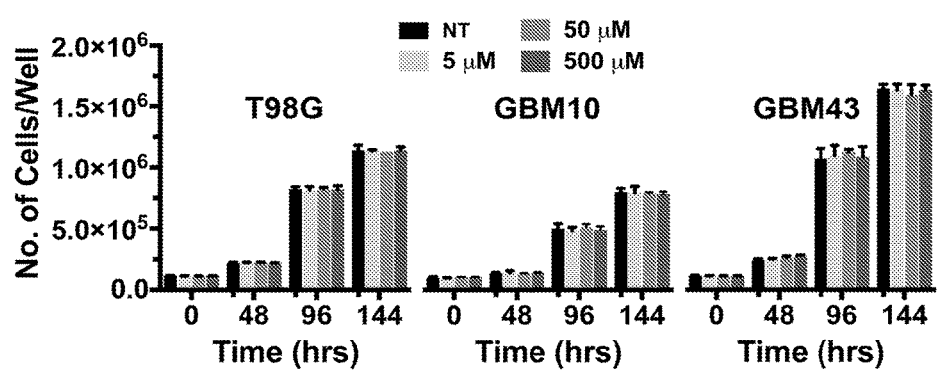
FIGS. 25A and 25B illustrate that PPF does not affect the proliferation in GBM cells.
Figure 25B:
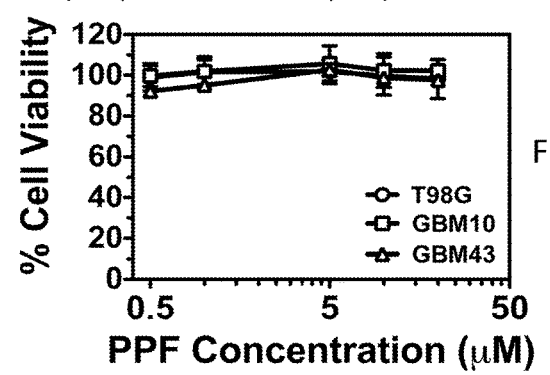

Referring now to FIGS. 25A and 25B: To determine if PPF influences glioma cell proliferation, the inventors treated T98G, GBM10, and GBM43 cells with increasing concentrations of PPF and evaluated cell proliferation over the course of 144 hours. Briefly, 1.25×10⁵ cells were seeded (n=3) in 12-well plates in 1 mL of DMEM supplemented with 10% FBS and allowed to attach at 37° for 16 hrs. Subsequently, the cells were treated with media alone, 5, 50, and 500 µM PPF. After 0, 48, 96 and 144 hours of treatment, the cells were trypsinized and counted using the automated cell counter. PPF did not affect the proliferation of glioma cells at doses up to 500 µM (FIG. 25A). The inventors also investigated whether PPF induces glioma cell cytotoxicity using CellTiterGlo® assay with increasing concentrations of PPF for 72 hours. Briefly, cells were seeded at a density of 3000 cells/well (100 µL) in 96 well plates. Increasing concentrations of PPF (0.5 to 20 µM) were added to the different wells (n=8) and incubated for 72 hours at 37° C. Subsequently, 100 µL of CellTiterGlo® reagent was added to each well and luminescence was measured using Envision Reader. On all 96 well plates, wells containing vehicle only or the positive control compound MG132 (a proteasome inhibitor) were also included. Raw values were normalized on a plate-by-plate basis such that 100% cell viability was equivalent to the mean of vehicle wells and 0% cell viability was equivalent to the mean of the MG132 positive control. The normalized data was used to assess viability of glioma cells after PPF treatment. Treatment with PPF resulted in a negligible loss of cell viability in all three GBM cell lines (FIG. 25B). Together, these data corroborate the published reports describing the limited side effect profile of PPF and demonstrate that, even at high doses, treatment with PPF does not cause toxicity in GBM cells (See Reference 39).

Referring now to FIGS. 26A, 26B, and 26C: Knockdown of TROY expression with shRNA decreases TMZ resistance in GBM cells in vitro (See Reference 42). To corroborate these results with pharmacological inhibition of TROY expression, the inventors tested whether the combination of PPF treatment and the current standard of care would result in enhanced therapeutic efficacy. Briefly, 5.0×10⁵ cells were seeded in 100-mm diameter culture dishes and incubated overnight at 37° C. Subsequently, cells were pre-treated with 5 µM PPF for 24 hours and then either treated with 250 µM TMZ for 24 hours or exposed to 2 Gy radiation dose using a RS 2000 X-ray irradiator. Following combination therapy, cells were trypsinized, counted, and plated in a 6-well culture dish at densities of 100, 250, and 500 cells per well in triplicate. Cells were incubated for 12 days then fixed, stained with 0.5% crystal violet solution, and counted manually by blinded observers. The inventors' results demonstrate that treatment with PPF in combination with TMZ significantly decreased the surviving fraction of T98G and GBM43 cells when compared to TMZ treatment alone (FIG. 26A). Similarly, combination treatment with PPF and 2Gy radiation significantly decreased the surviving fraction of GBM cells when compared to 2Gy radiation alone (FIG. 26A). Next, to test whether the decrease in survival was due to an increase in apoptosis, the inventors isolated lysate from T98G glioma cells after treatment with vehicle, PPF alone, TMZ alone, and PPF in combination with TMZ and immunoblotted for cleaved PARP. The inventors found that T98G cells exposed to the combination treatment of PPF and TMZ showed an increase in cleaved PARP as compare to TMZ treatment alone (FIG. 26B). Since TROY-mediated therapeutic resistance is dependent upon activation of the AKT and NF-κB signaling pathways (See Reference 42), the inventors investigated the effect of PPF on TROY survival signaling. T98G and GBM43 cells were treated with PPF, lysed, and then immunoblotted to assess the activation of AKT and NF-κB. PPF effectively decreased AKT and NF-κB phosphorylation in both cell lines (FIG. 26C). These data validate that PPF inhibits TROY survival signaling pathways and augments the efficacy of TMZ in GBM.

Figure 27A:
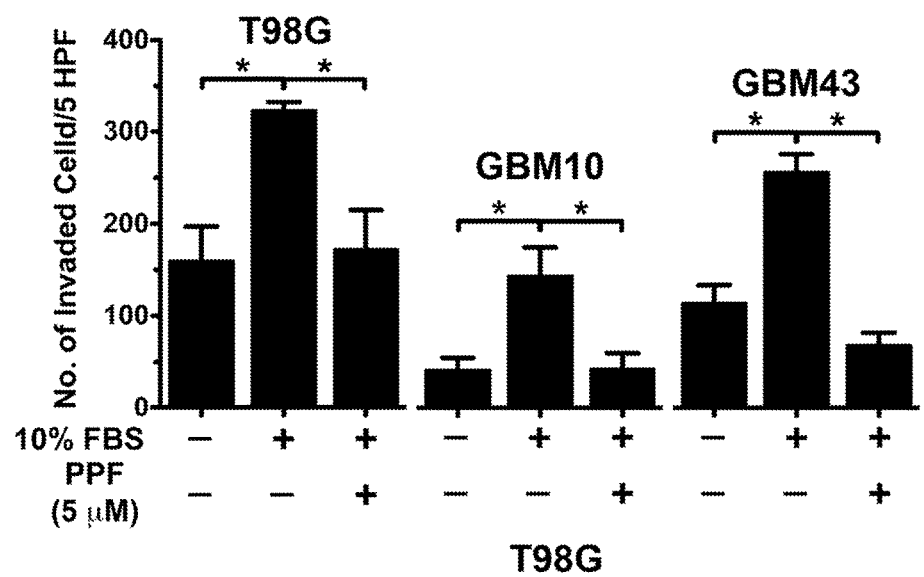
FIGS. 27A and 27B depict that PPF suppresses GBM cell invasion and Rac1 activation.
Figure 27B:
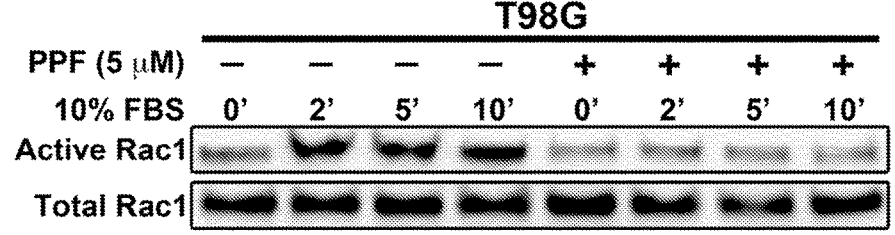

Referring now to FIGS. 27A and 27B: The inventors next examined whether PPF inhibited TROY dependent glioma cell invasion. T98G, GBM10, and GBM43 glioma cells were treated with PPF, and using a Matrigel invasion assay, the inventors demonstrated that treatment with 5 µM PPF significantly inhibited glioma cell invasion in vitro (FIG. 27A). Briefly, 5.0×10⁵ glioma cells were seeded in 100-mm diameter culture dishes and incubated overnight at 37° C. Subsequently, cells were serum starved for 16 hours at 37° C. Cells were then harvested, re-suspended in growth factor reduced Matrigel (Becton Dickinson) (1.0×10⁵ cells/50 uL), added in triplicates to collagen-coated transwell chambers, and allowed to invade through Matrigel in presence of 10% FBS and/or 5 µM PPF. After incubation for 24 hours at 37° C., non-invaded cells were scrapped off the upper side of the membrane and cells invaded to the other side of the membrane were fixed with 4% paraformaldehyde (PFA) (Affymetrix) and stained with DAPI (Invitrogen). Nuclei of invaded cells were counted in five high power fields (HPF) with a 20× objective. TROY-mediated invasion is induced, in part, through activation of Rac1, and the inventors' results showed that PPF inhibited Rac1 activation in T98G cells (FIG. 27B) (See Reference 43).

Figure 28A:
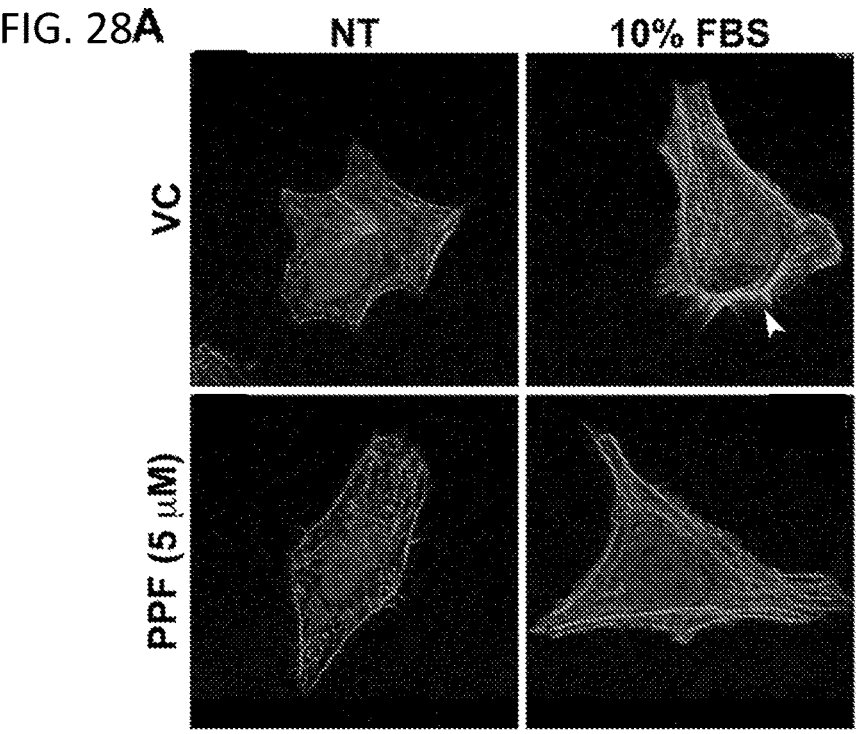
FIGS. 28A and 28B depict that PPF suppresses GBM cell membrane ruffling.
Figure 28B:
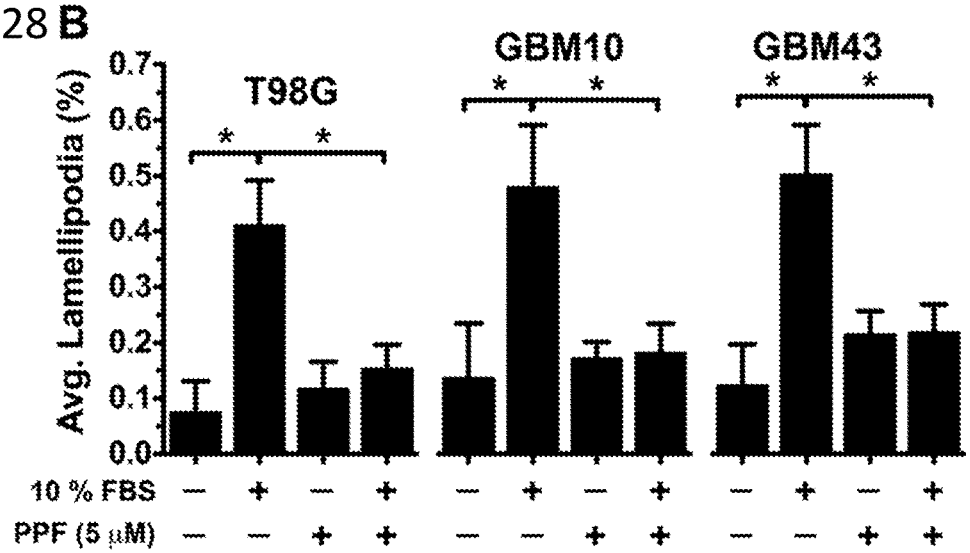

Referring now to FIGS. 28A and 28B: The inventors investigated lamellipodia formation and membrane ruffling. Briefly, glioma cells were plated onto 10-well glass slides pre-coated with 10 µg/ml laminin at the density of 3000 cells/well for 24 hours at 37° C. Subsequently, cells were serum starved for 16 hours. The cells were pre-incubated with 5 µM PPF or vehicle for 1 hour prior to 10% FBS stimulation for 5 min. After FBS stimulation, cells were fixed in 4% PFA, permeabilized with 0.1% Triton X-100, and incubated with Alexa Fluor® 555 Phalloidin (Invitrogen) to stain for F-actin. Slides were mounted with ProLong® reagent with DAPI and imaged using a Zeiss LSM 510 microscope. For each experimental condition, at least 12 images were randomly taken. Lamellipodia were traced using ImageJ software. For each cell, the fraction of the cell perimeter that displayed lamellipodia was calculated. The inventors evaluated lamellipodia formation after PPF treatment in T98G, GBM10, and GBM43, cells, and showed that PPF significantly decreased lamellipodia formation and membrane ruffling (FIGS. 28A and 28B).

REFERENCES

So as to reduce the complexity and length of the Detailed Specification, Inventors herein expressly incorporate by reference to the extent applicable, all of the following materials.

1. 2007-2008 Primary Brain Tumors in the United States Statistical Report, Central Brain Tumor Registry of the United States, (2008).
2. Macdonald D R, Semin Oncol 30, 72-76 (2003).
3. Salhia B et al, Expert Rev Mol Diagn 6, 613-626 (2006).
4. Giese A et al, J Clin Oncol 21, 1624-1636 (2003).
5. Hu S et al, Genomics 62, 103-107 (1999).
6. Park J B et al, Neuron 45, 345-351 (2005).
7. Pipsa J et al, Gene Expr Patterns 3 675-679 (2003).
8. Hisaoka T et al, Glia 45, 313-324 (2004).
9. Shao Z et al, Neuron 45, 353-359 (2005).
10. Hisaoka T et al, Brain Res Dev Brain Res 143, 105-109 (2003).
11. Maher E A et al, Genes Dev 15, 1311-1333 (2001).

12. Castro M G et al, Pharmacol Ther 98, 71-108 (2003).
13. Rich J N and Bigner D D, Nat Rev Drug Discov 3, 430-446 (2004).
14. Bredel M et al, J Am Med Assoc 302, 261-275 (2009).
15. Parsons D W et al, Science 321, 1807-1812 (2008).
16. Lesniak M S and Brem H, Nat Rev Drug Discov 3, 499-508, (2004).
17. Tysnes B B and Mahesparan R, J Neurooncol 53, 129-147 (2001).
18. Friedl P and Wolf K, Nat Rev Cancer 3, 362-374 (2003).
19. Joy A M et al, J Cell Sci 116, 4409-4417 (2003).
20. Eby M T et al, J Biol Chem 275, 15336-15342 (2000).
21. Spanjaard R A et al, Int J Cancer 120, 1304-1310 (2007).
22. Chan A Y et al, Oncogene 24, 7821-7829 (2005).
23. Chuang Y Y et al, Cancer Res 64, 8271-8275 (2004).
24. Tran N L et al, Cancer Res 66, 9535-9542 (2006).
25. Nakada M et al, Cancer Res 66, 8492-8500 (2006).
26. Lipinski C A et al, J Neuro-Oncol 90, 181-189 (2008).
27. Berens M E et al, Clin Exp Metastasis 12, 405-415 (1994).
28. McDonough W S et al, Neoplasia 7, 862-872 (2005).
29. Hashimoto T et al, Cell Cycle 7, 106-111 (2008).
30. Jarazynka M J et al, Cancer Res 67, 7203-7211 (2007).
31. Taillandier L et al, J Neurosci Methods 125, 147-157 (2003).
32. Wilcox M E et al, J Natl Cancer Inst 93, 903-912 (2001).
33. Mahesparan R et al, Acta Neuropathol (Berl) 105, 49-57 (2003).
34. Sarkaria J N et al, Clin Cancer Res 12, 2264-2271 (2006).
35. Sarkaria J N et al, Mol Cancer Ther 6, 1167-1174 (2007).
36. Pandita A et al, Genes Chromosomes Cancer 39, 29-36 (2004).
37. Mielke R et al, Alzheimer Dis Assoc Disord 12 Suppl 2, 29-35 (1998).
38. Rother M et al, Dement Geriatr Congn Disord 9 Suppl 1, 36-43 (1998).
39. Sweitzer S et al, Handb Exp Pharmacol 200, 235-250 (2011).
40. Jacobs V et al, Neuro-Oncolgy 14, 119-131 (2012).
41. Jacobs V et al, PLoS One 7 (2012).
42. Loftus J et al, Mol Cancer Res 11, 865-874 (2013).
43. Paulino V et al, Mol Cancer Res 8, 1558-1567 (2010).

The invention claimed is:

1. A pharmaceutical composition comprising:
a first active ingredient, wherein the first active ingredient is propentofylline or a pharmaceutically acceptable salt thereof; and
a second active ingredient, wherein the second active ingredient is a chemotherapeutic agent selected from the group consisting of: cis-diamminedichloro platinum (II) (cisplatin), doxorubicin, 5-fluorouracil, paclitaxel, topoisomerase inhibitor, and a targeted-therapy drug.

2. The pharmaceutical composition of claim 1, wherein the topoisomerase inhibitor is selected from the group consisting of: etoposide, teniposide, irinotecan, and topotecan.

3. The pharmaceutical composition of claim 1, wherein the targeted-therapy drug is selected from the group consisting of: an inhibitor of signaling through TROY (TNFRSF19) activation, temozolomide, bevacizumab, gefitinib, erlotinib, cetuximab, lapatinib, panitumumab, vandetanib, afatinib, icotinib, zalutumumab, nimotuzumab, and matuzumab.

4. The pharmaceutical composition of claim 3, wherein the inhibitor of signaling through TROY (TNFRSF19) activation is selected from the group consisting of: Pyk2 inhibitors, Rac1 inhibitors, Dock180 inhibitors, and Dock7 inhibitors.

5. The pharmaceutical composition of claim 1, wherein the second active ingredient is selected from the group consisting of: Pyk2 inhibitors, Rac1 inhibitors, Dock180 inhibitors, Dock7 inhibitors, temozolomide, and bevacizumab.

6. The pharmaceutical composition of claim 1, wherein the second active ingredient is selected from the group consisting of: an antibody against TROY that inhibits TROY, Pyk2 shRNA, Rac1 siRNA, Dock180 siRNA, Dock7 siRNA, temozolomide, and bevacizumab.

7. The pharmaceutical composition of claim 1, wherein the second active ingredient is temozolomide.

8. The pharmaceutical composition of claim 1 further comprising at least one pharmaceutically acceptable carrier.

9. The pharmaceutical composition of claim 1, wherein the composition treats glioblastoma.

10. The pharmaceutical composition of claim 8, wherein the propentofylline or a pharmaceutically acceptable salt thereof is in an amount sufficient to inhibit TROY expression, but the amount is less than sufficient to substantially reduce viability of glioblastoma cells.

11. The pharmaceutical composition of claim 9, further comprising an anxiolytic agent.

12. The pharmaceutical composition of claim 1, further comprising an antiemetic ingredient.

13. The pharmaceutical composition of claim 1, further comprising a hematopoietic colony stimulating factor.

14. The pharmaceutical composition of claim 1, further comprising an analgesic agent.

* * * * *